US011602335B2

(12) United States Patent
Nock

(10) Patent No.: US 11,602,335 B2
(45) Date of Patent: Mar. 14, 2023

(54) CORE NEEDLE BIOPSY DEVICE FOR COLLECTING MULTIPLE SAMPLES IN A SINGLE INSERTION

(71) Applicant: Devicor Medical Products, Inc., Cincinnati, OH (US)

(72) Inventor: Andrew Paul Nock, Dayton, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 420 days.

(21) Appl. No.: 16/381,573

(22) Filed: Apr. 11, 2019

(65) Prior Publication Data

US 2019/0231325 A1 Aug. 1, 2019

Related U.S. Application Data

(63) Continuation of application No. PCT/US2017/056123, filed on Oct. 11, 2017.
(Continued)

(51) Int. Cl.
*A61B 10/02* (2006.01)

(52) U.S. Cl.
CPC .. *A61B 10/0275* (2013.01); *A61B 2010/0208* (2013.01); *A61B 2010/0225* (2013.01)

(58) Field of Classification Search
CPC . A61B 10/0275; A61B 5/0233; A61B 5/0266; A61B 5/0275; A61B 2010/0208;
(Continued)

(56) References Cited

U.S. PATENT DOCUMENTS

| 5,511,556 A | 4/1996 | DeSantis |
| 5,526,822 A | 6/1996 | Burbank et al. |

(Continued)

FOREIGN PATENT DOCUMENTS

| JP | H11-506634 | 6/1995 |
| JP | 2004-535837 | 12/2004 |

(Continued)

OTHER PUBLICATIONS

International Search Report and Written Opinion dated Mar. 14, 2018 for International Application No. PCT/US2017/056123, 14 pages.

(Continued)

*Primary Examiner* — Nathan J Jenness
*Assistant Examiner* — Severo Antonio P Lopez
(74) *Attorney, Agent, or Firm* — Frost Brown Todd LLP

(57) ABSTRACT

A core needle biopsy device including a needle assembly, a cutter drive assembly, a piercer drive assembly and a piercer retraction assembly. The needle assembly includes a piercer and a hollow cutter. The piercer includes a sharp distal tip and a notch proximal to the distal tip. The piercer is slidably disposed within the cutter to sever a tissue sample into the notch. The cutter drive assembly is configured to selectively fire the cutter. The piercer drive assembly is configured to selectively fire the piercer. The piercer retraction assembly is configured to retract the piercer independently of the cutter while the needle assembly is disposed within a patient to expose the notch of the piercer to an exterior of a patient.

19 Claims, 23 Drawing Sheets

Related U.S. Application Data

(60) Provisional application No. 62/407,201, filed on Oct. 12, 2016.

(58) Field of Classification Search
CPC ........ A61B 2010/0225; A61B 10/0283; A61B 10/0266; A61B 10/0096; A61B 10/02; A61B 10/0233
See application file for complete search history.

(56) References Cited

U.S. PATENT DOCUMENTS

| | | | |
|---|---|---|---|
| 5,560,373 A | | 10/1996 | DeSantis |
| 5,817,033 A | | 10/1998 | DeSantis et al. |
| 5,928,164 A | | 7/1999 | Burbank et al. |
| 5,971,939 A | | 10/1999 | DeSantis et al. |
| 6,017,316 A | | 1/2000 | Ritchart et al. |
| 6,086,544 A | | 4/2000 | Hibner et al. |
| 6,162,187 A | | 12/2000 | Buzzard et al. |
| 6,432,065 B1 | | 8/2002 | Burdorff et al. |
| 6,626,849 B2 | | 9/2003 | Huitema et al. |
| 6,752,768 B2 | | 6/2004 | Burdorff et al. |
| 7,226,459 B2 | * | 6/2007 | Cesarini ........... A61B 17/32002 |
| 7,442,171 B2 | | 10/2008 | Stephens et al. |
| 7,648,466 B2 | | 1/2010 | Stephens et al. |
| 7,837,632 B2 | | 11/2010 | Stephens et al. |
| 7,854,706 B2 | | 12/2010 | Hibner |
| 7,914,464 B2 | | 3/2011 | Burdorff et al. |
| 7,938,786 B2 | | 5/2011 | Ritchie et al. |
| 8,083,687 B2 | | 12/2011 | Parihar |
| 8,118,755 B2 | | 2/2012 | Hibner et al. |
| 8,206,316 B2 | | 6/2012 | Hibner et al. |
| 8,241,226 B2 | | 8/2012 | Hibner et al. |
| 8,337,415 B2 | * | 12/2012 | Trezza, II ...... A61B 17/320016 600/567 |
| 8,454,531 B2 | | 6/2013 | Speeg et al. |
| 8,622,924 B2 | | 1/2014 | Speeg et al. |
| 8,702,623 B2 | | 4/2014 | Parihar et al. |
| 8,764,680 B2 | | 7/2014 | Rhad et al. |
| 8,801,742 B2 | | 8/2014 | Rhad et al. |
| 8,858,465 B2 | | 10/2014 | Fiebig |
| 8,938,285 B2 | | 1/2015 | Fiebig et al. |
| 9,095,326 B2 | | 8/2015 | Ritchie et al. |
| 9,326,755 B2 | | 5/2016 | Fiebig et al. |
| 9,345,457 B2 | | 5/2016 | Speeg et al. |
| 2002/0065474 A1 | | 5/2002 | Viola |
| 2006/0074345 A1 | | 4/2006 | Hibner |
| 2009/0131821 A1 | | 5/2009 | Speeg et al. |
| 2010/0152610 A1 | | 6/2010 | Parihar et al. |
| 2010/0160819 A1 | | 6/2010 | Parihar et al. |
| 2011/0054350 A1 | * | 3/2011 | Videbaek ........... A61B 10/0275 600/568 |
| 2013/0324882 A1 | | 12/2013 | Mescher |
| 2014/0371585 A1 | | 12/2014 | Thompson et al. |
| 2020/0187919 A1 | * | 6/2020 | Long ................. A61B 10/0275 |

FOREIGN PATENT DOCUMENTS

| | | |
|---|---|---|
| JP | 2005-103276 | 4/2005 |
| JP | 2009-505696 | 2/2009 |
| JP | 2009-532081 | 9/2009 |
| WO | WO 2007/112751 A2 | 10/2007 |

OTHER PUBLICATIONS

Hahn, M., et al., "Diagnostic Primer: Vacuum-Assisted Breast Biopsy with Mammotome®," Devicor Medical Germany GmBh, Nov. 11, 2012, Germany, Springer Medizin Verlag, copyright 2013, 130 pgs.

European Communication dated Nov. 26, 2020 for Application No. 17791244.1, 8 pages.

European Communication dated Apr. 9, 2021 for Application No. 17791244.1, 6 pages.

Japanese Office Action dated Jun. 29, 2021 for Application No. 2019-519761, 8 pages.

* cited by examiner

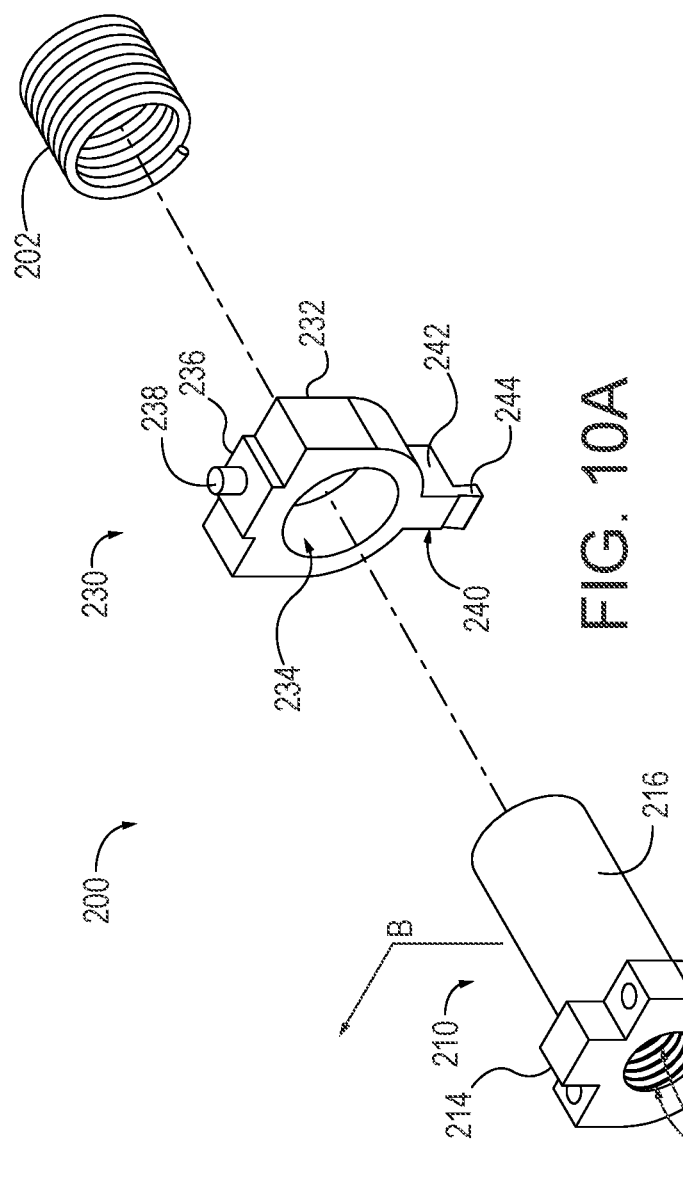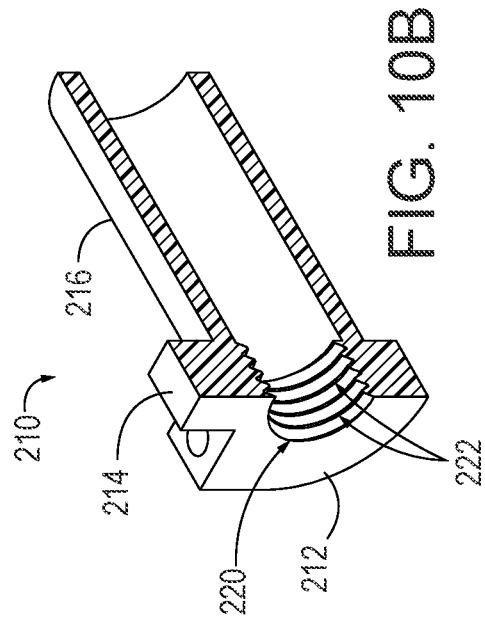

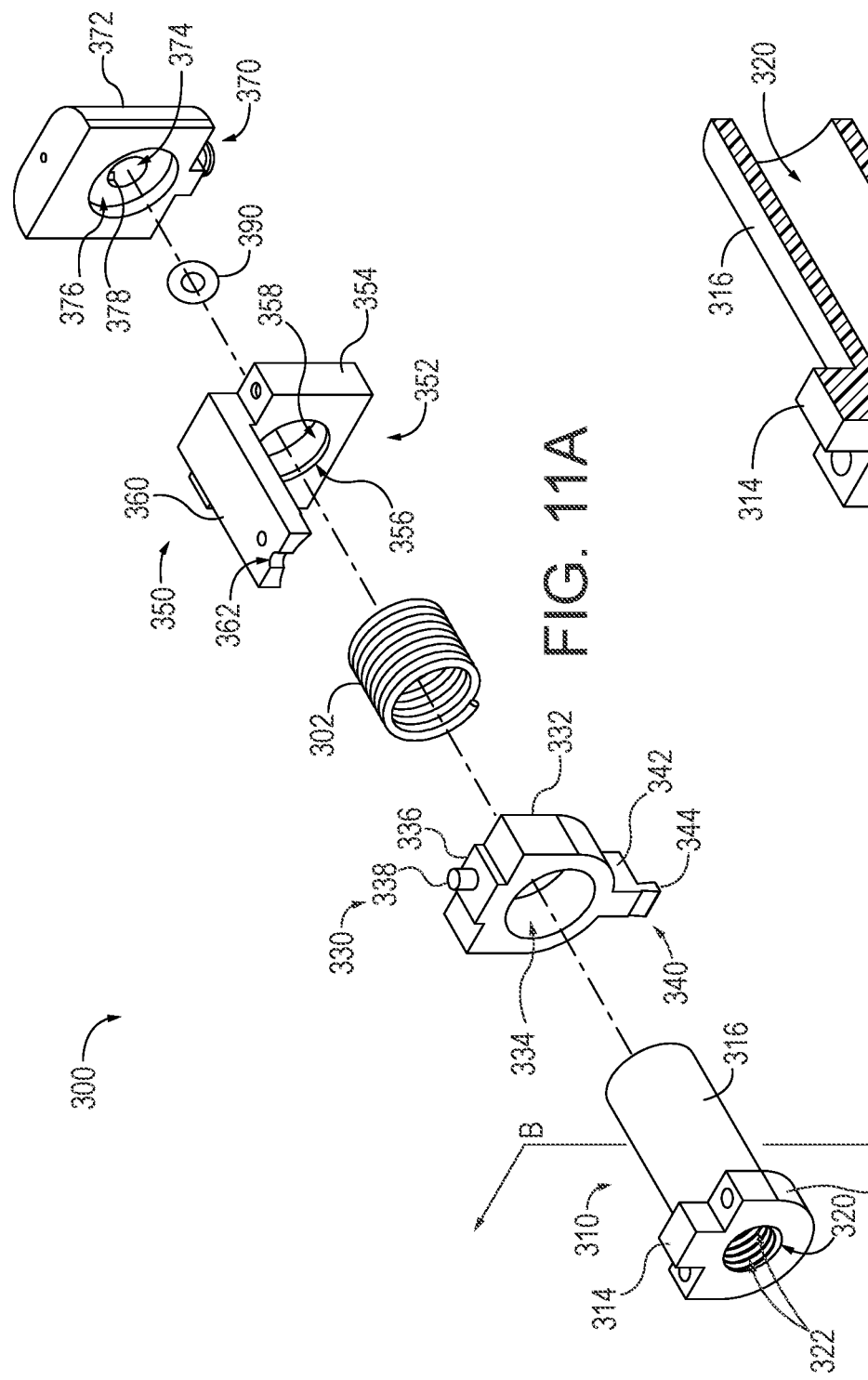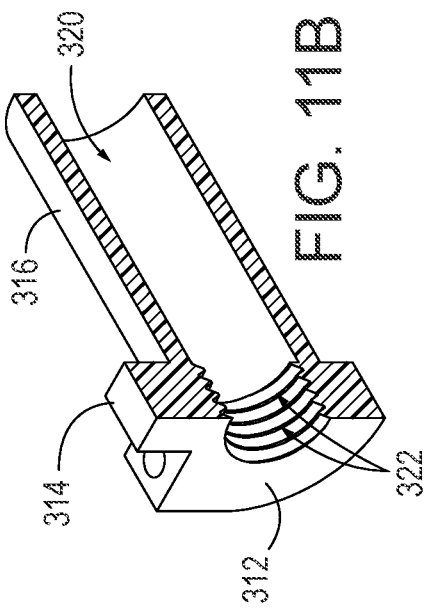

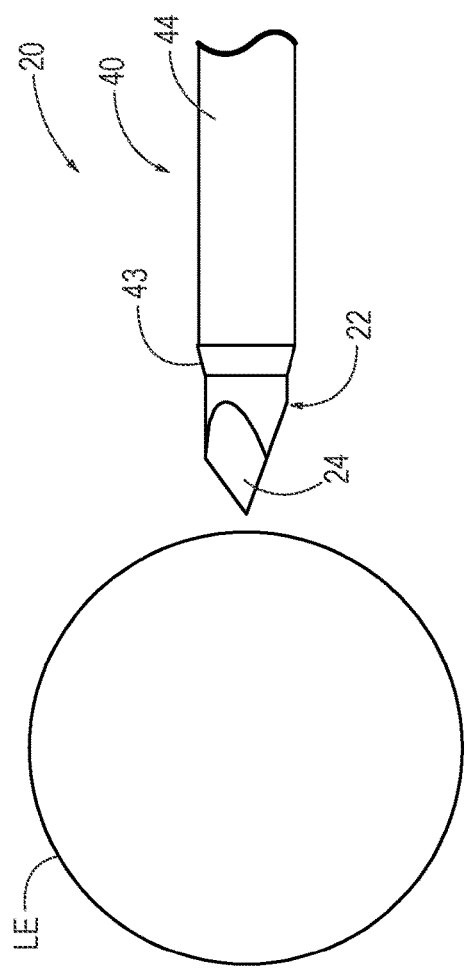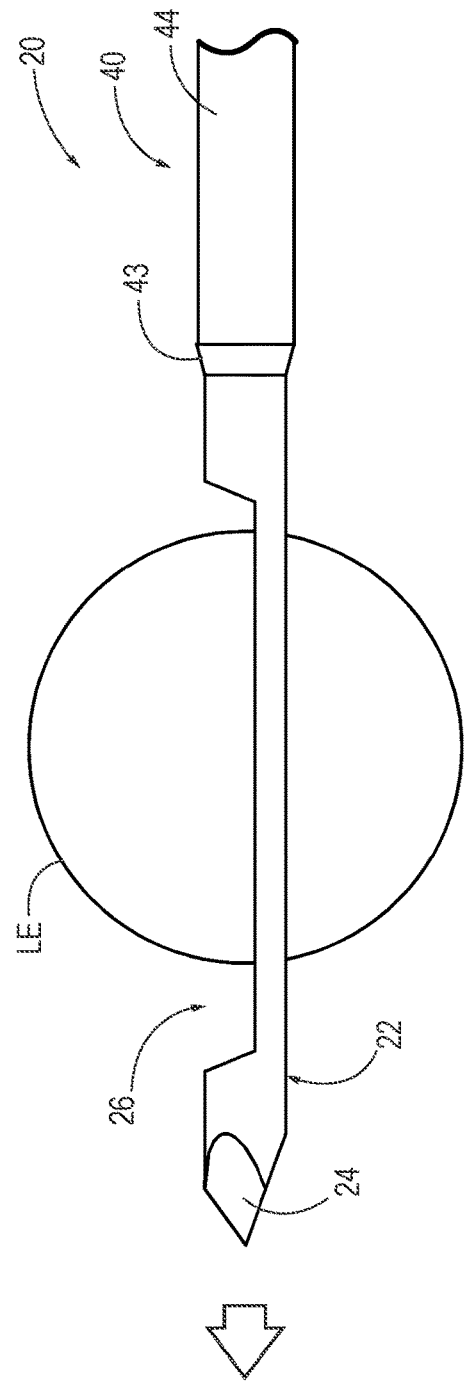
FIG. 19
FIG. 20

CORE NEEDLE BIOPSY DEVICE FOR COLLECTING MULTIPLE SAMPLES IN A SINGLE INSERTION

PRIORITY

The present application is a continuation of International Application No. PCT/US2017/056123, entitled "CORE NEEDLE BIOPSY DEVICE FOR COLLECTING MULTIPLE SAMPLES IN A SINGLE INSERTION," filed Oct. 11, 2017, which claims priority to U.S. Provisional Patent Application No. 62/407,201, entitled "CORE NEEDLE BIOPSY DEVICE FOR COLLECTING MULTIPLE SAMPLES IN A SINGLE INSERTION," filed on Oct. 12, 2016, the disclosure of which is hereby incorporated by reference.

BACKGROUND

A biopsy is the removal of a tissue sample from a patient to enable examination of the tissue for signs of cancer or other disorders. Tissue samples may be obtained in a variety of ways using various medical procedures involving a variety of the sample collection devices. For example, biopsies may be open procedures (surgically removing tissue after creating an incision) or percutaneous procedures (e.g. by fine needle aspiration, core needle biopsy, or vacuum assisted biopsy). After the tissue sample is collected, the tissue sample is typically analyzed at a lab (e.g. a pathology lab, biomedical lab, etc.) that is set up to perform the appropriate tests (such as histological analysis).

Biopsy samples have been obtained in a variety of ways in various medical procedures including open and percutaneous methods using a variety of devices. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

One technique for collecting a breast biopsy is to use a core needle biopsy device. One such device is the MAX-CORE disposable core biopsy instrument manufactured by Bard Biopsy Systems. Core needle biopsy devices frequently use a sharp, solid piercer equipped with a lateral tissue receiving notch positioned adjacent to the distal end of the piercer. When tissue is received within the notch, an elongate hollow cutting sheath is translated over the notch to sever a tissue sample. The severed tissue sample is then stored within the notch until both the piercer and the cutting sheath are removed from the patient. Thus, in core-needle biopsy devices, only one tissue sample can be collected per insertion of the piercer and cutting sheath.

Another technique for conducting a breast biopsy is to conduct a breast biopsy using a vacuum-assisted breast biopsy device. A current textbook in this area is "Vacuum-Assisted Breast Biopsy with Mammotome®" available Nov. 11, 2012, copyright 2013 by Devicor Medical Germany GmBh, published in Germany by Springer Medizin Verlag, Authors: Markus Hahn, Anne Tardivon and Jan Casselman, ISBN 978-3-642-34270-7.

In contrast to core needle breast biopsy procedures, state of the art vacuum-assisted breast biopsy devices permit the probe to remove multiple samples without requiring the probe be removed from the breast after every sample is collected. For instance, in a vacuum assisted breast biopsy device, a hollow needle is used to penetrate tissue. The hollow needle includes a lateral aperture adjacent to a sharp distal tip. A hollow cutter is disposed within the hollow needle and is moved axially relative to the lateral aperture of the needle to sever tissue samples. Once a tissue sample is severed by the hollow cutter, the tissue sample is transported axially though the cutter and collected in a tissue collection feature.

Examples of vacuum assisted biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; U.S. Pat. No. 8,118,755, entitled "Biopsy Sample Storage," issued Feb. 1, 2012; U.S. Pat. No. 8,206,316, entitled "Tetherless Biopsy Device with Reusable Portion," issued on Jun. 26, 2012; U.S. Pat. No. 8,702,623, entitled "Biopsy Device with Discrete Tissue Chambers," issued on Apr. 22, 2014; U.S. Pat. No. 8,858,465, entitled "Biopsy Device with Motorized Needle Firing," issued Oct. 14, 2014; and U.S. Pat. No. 9,326,755, entitled "Biopsy Device Tissue Sample Holder with Bulk Chamber and Pathology Chamber," issued May 3, 2016. The disclosure of each of the above-cited U.S. patents is incorporated by reference herein.

Additional examples of vacuum assisted biopsy devices and biopsy system components are disclosed in U.S. Pub. No. 2006/0074345, entitled "Biopsy Apparatus and Method," published Apr. 6, 2006 and now abandoned; U.S. Pub. No. 2009/0131821, entitled "Graphical User Interface for Biopsy System Control Module," published May 21, 2009, now abandoned; U.S. Pub. No. 2010/0152610, entitled "Hand Actuated Tetherless Biopsy Device with Pistol Grip," published Jun. 17, 2010, now abandoned; U.S. Pub. No. 2010/0160819, entitled "Biopsy Device with Central Thumbwheel," published Jun. 24, 2010, now abandoned; and U.S. Pub. No. 2013/0324882, entitled "Control for Biopsy Device," published Dec. 5, 2013. The disclosure of each of the above-cited U.S. patent application Publications is incorporated by reference herein.

Exemplary core needle biopsy devices are disclosed in U.S. Pat. No. 5,560,373, entitled "Needle Core Biopsy Instrument with Durable or Disposable Cannula Assembly," issued on Oct. 1, 1996; U.S. Pat. No. 5,817,033, entitled "Needle Core Biopsy Device," issued on Oct. 6, 1998; U.S. Pat. No. 5,971,939, entitled "Needle Core Biopsy Device,"

issued on Oct. 26, 1999; and U.S. Pat. No. 5,511,556, entitled "Needle Core Biopsy Instrument," issued on Apr. 30, 1996. The disclosure of each of the above-cited U.S. patents is incorporated by reference herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIG. 10A depicts an exploded view of a cutter drive assembly of the drive assembly of FIG. 4;

FIG. 10B depicts a cross-sectional view of a cocking member of the cutter drive assembly of FIG. 10A, the cross-section taken along line B-B of FIG. 10A;

FIG. 11A depicts an exploded view of a piercer drive assembly of the drive assembly of FIG. 4;

FIG. 11B depicts a cross-sectional view of a cocking member of the piercer drive assembly of FIG. 11A, the cross-section taken along line B-B of FIG. 11A;

FIG. 19 depicts a partial front elevational view of the needle assembly of FIG. 2, with the needle assembly positioned adjacent to a lesion;

FIG. 20 depicts another partial front elevational view of the needle assembly of FIG. 2, with a piercer fired through the lesion;

Figure 1:
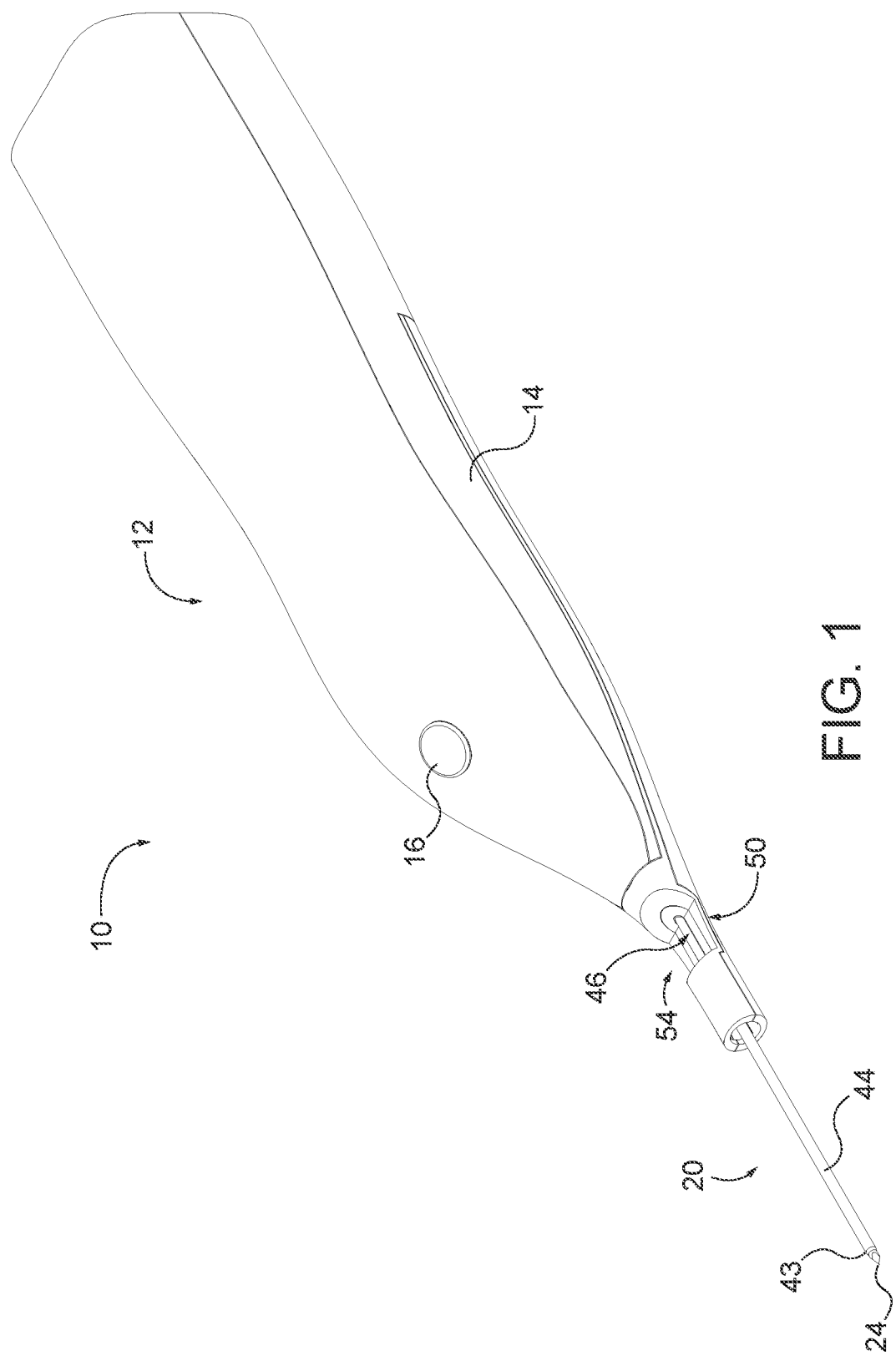
FIG. 1 depicts a perspective view of an exemplary core needle biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Biopsy devices may be used to collect tissue samples in a variety of ways. For example, in some instances tissue samples are collected into a single tissue basket such that all tissue samples collected during a given biopsy procedure are deposited into the single tissue sample basket. In some other instances, tissue samples are collected into a tissue sample holder having separate compartments for each collected tissue sample. Such a multi-compartment tissue sample holder may additionally include trays or strips that individually hold each tissue sample separately from the other tissue samples. Such trays or strips may be removable or otherwise separable from the tissue sample holder at the conclusion of a biopsy procedure.

Regardless of the structure in which the tissue samples are stored, tissue samples may be collected using biopsy devices under the guidance of various imaging modalities such as ultrasound image guidance, stereotactic (X-ray) guidance, MRI guidance, Positron Emission Mammography ("PEM" guidance), Breast-Specific Gamma Imaging ("BSGI") guidance, or otherwise. Each procedure has its own methodology based on the form of imaging guidance used. The following text briefly describes ultrasound image guided biopsy procedures, stereotactic guided biopsy procedures and MRI guided biopsy procedures.

In an ultrasound image guided breast biopsy procedure, the operator may position an ultrasound transducer on the patient's breast and maneuver the transducer while viewing an ultrasound image display screen to locate suspicious tissue in the patient's breast. Once the operator locates the suspicious tissue, the operator may anesthetize the target region of the breast. Once the breast has been anesthetized, the operator may create an initial incision using a scalpel at a location on the exterior of the breast offset from the transducer. A needle of a breast biopsy probe disposed coaxially within an introducer cannula is then inserted into the breast through the initial incision. The operator continues to hold the ultrasound transducer with one hand while maneuvering the biopsy probe with the other hand. While viewing the ultrasound image on the display screen, the operator guides the needle to a position adjacent to the suspicious tissue. A cutter within the needle of the probe is used to remove tissue which is then conveyed either to a manual pick-up location on the breast biopsy device or to a tissue sample chamber. The needle of the breast biopsy device is then removed, leaving the introducer cannula disposed within the breast. The introducer cannula may then be used to introduce a biopsy marker cannula for deploying a biopsy site marker at the biopsy site. Once a marker has been deployed at the biopsy site, the biopsy marker cannula and the introducer cannula are both removed from the breast and the incision is closed using a medically acceptable way to close breaks in the skin.

In a stereotactic image guided breast biopsy procedure, the patient is first positioned relative to x-ray equipment, which includes a breast localization assembly. In some procedures, the patient is oriented in a prone position, with the patient lying face down on a procedure table with at least one breast hanging pendulously through an aperture in the procedure table. The breast is then compressed between a compression paddle and an x-ray receptor of a localization assembly that is positioned under the procedure table. A breast biopsy device is positioned on an automatic guide device in front of the compression paddle and between the breast and an x-ray source. Once positioning of the patient and localization of the breast are complete, a scout image is acquired with the x-ray receptor in a zero-degree angular position (i.e., the x-rays are emitted along an axis normal relative to the x-ray receptor). If the scout image indicates that the patient has been positioned in a desired position, the procedure may proceed with the acquisition of stereotactic image pairs. Stereotactic image pairs are acquired by orienting the x-ray source at various complementary angular positions relative to the x-ray receptor (e.g., +15° and −15°), with at least one x-ray image acquired at each position.

Further in the stereotactic image guided breast biopsy procedure, once a suitable stereotactic image pair is acquired, an operator may identify a target site where biopsy sampling is desired by examining the stereotactic image pair. The target site is marked on each stereotactic image and a precise location of the target site on a Cartesian coordinate system is computed using an image processing module. The computed location of the target site is then communicated to the automatic guide device. The automatic guide device is responsive to this information to position the breast biopsy probe into a position that aligns with the target site. With the breast biopsy device positioned, an operator may then fire a needle of the biopsy probe into the breast of the patient, thereby positioning the needle at the target site. A cutter within the needle of the probe is used to remove tissue, which is then conveyed either to a manual pick-up location on the breast biopsy device or to a tissue sample chamber. After the biopsy tissue is removed, a biopsy marker cannula is inserted into the needle and is used to deploy a biopsy site marker at the biopsy site. Once a marker has been deployed at the biopsy site, the needle is removed from the breast and the incision is closed using a medically acceptable way to close breaks in the skin.

In an MRI guided breast biopsy procedure, after the patient is properly positioned on the table and a targeting device (e.g., a grid and cube combination or a pillar, post and cradle support combination) has been deployed and used, a baseline MRI image is taken to verify the target location. After that, a scalpel is used to incise the skin of the breast. Next, an assembly, formed by an obturator disposed in a sleeve, is inserted through the incision to penetrate the breast tissue under the skin. In some acceptable surgical techniques, the obturator is removed and an imaging rod is inserted into the sleeve in place of the obturator. An imaging rod is defined simply as an appropriately shaped rod that includes a feature that is detectable by an imaging technique being used for the biopsy procedure. The MRI image of the imaging rod is used to locate the site to which the sleeve/obturator assembly has penetrated. In some other acceptable surgical techniques, the obturator cooperates with the breast tissue to provide a visually observable artifact in an MRI image. With both of these techniques, after the location within the breast where the biopsy is to be taken is confirmed, the obturator or the imaging rod is removed.

Further in the MRI guided breast biopsy procedure, after the obturator or imaging rod has been removed, it is replaced in the sleeve with the needle of a breast biopsy probe. A cutter within the needle of the probe is used to remove tissue, which is then conveyed either to a manual pick up location on the breast biopsy device or to a breast biopsy device sample chamber. After the biopsy tissue is removed, a biopsy marker cannula is inserted into the needle and is used to deploy a biopsy site marker at the biopsy site. The needle is then removed from the sleeve. Optionally, the imaging rod or the obturator is put back into the breast for reimaging of the biopsy site. Then the imaging rod or obturator and the sleeve are removed.

Vacuum assisted biopsy devices and core needle biopsy devices both may have various advantages over the other, depending on context. For instance, one advantage of vacuum assisted biopsy devices is that vacuum assistance permits removal of multiple tissue samples using a single insertion. However, while core needle biopsy devices lack this feature, use of core needle biopsy devices may still be desirable. For instance, core needle biopsy devices are generally capable of having smaller needles relative to core needle biopsy devices, thereby reducing patient anxiety and increasing the capacity of the needle to penetrate a lesion. Therefore, in some instances it may be desirable to incorporate the feature of multiple sample removal of a vacuum assisted biopsy device into a core needle biopsy device to achieve the benefits present in both styles of biopsy device.

A desirable feature of the device described herein, which is a core needle biopsy device is that the device allows for single insertion with multiple samples being obtained whilst using a core needle type device. Currently, it is believed that only vacuum assisted biopsy devices have this ability.

FIG. 1 shows an exemplary core needle biopsy device (10) for use in a breast biopsy procedure. Core needle biopsy device (10) of the present example comprises a body (12) and a needle assembly (20) extending distally from body (12). Body (12) includes an outer housing (14) and an actuation member (16) disposed on outer housing (14). As will be describe in greater detail below, outer housing (14)

encloses various components of biopsy device (10), which are used to drive needle assembly (20) through a cutting cycle and a tissue acquisition cycle. To this end, outer housing (14) of the present example is sized and shaped for grasping by an operator using a single hand. Although not shown, it should be understood that in some examples outer housing (14) may comprise multiple parts such that each part interconnects to form outer housing (14).

Figure 2:
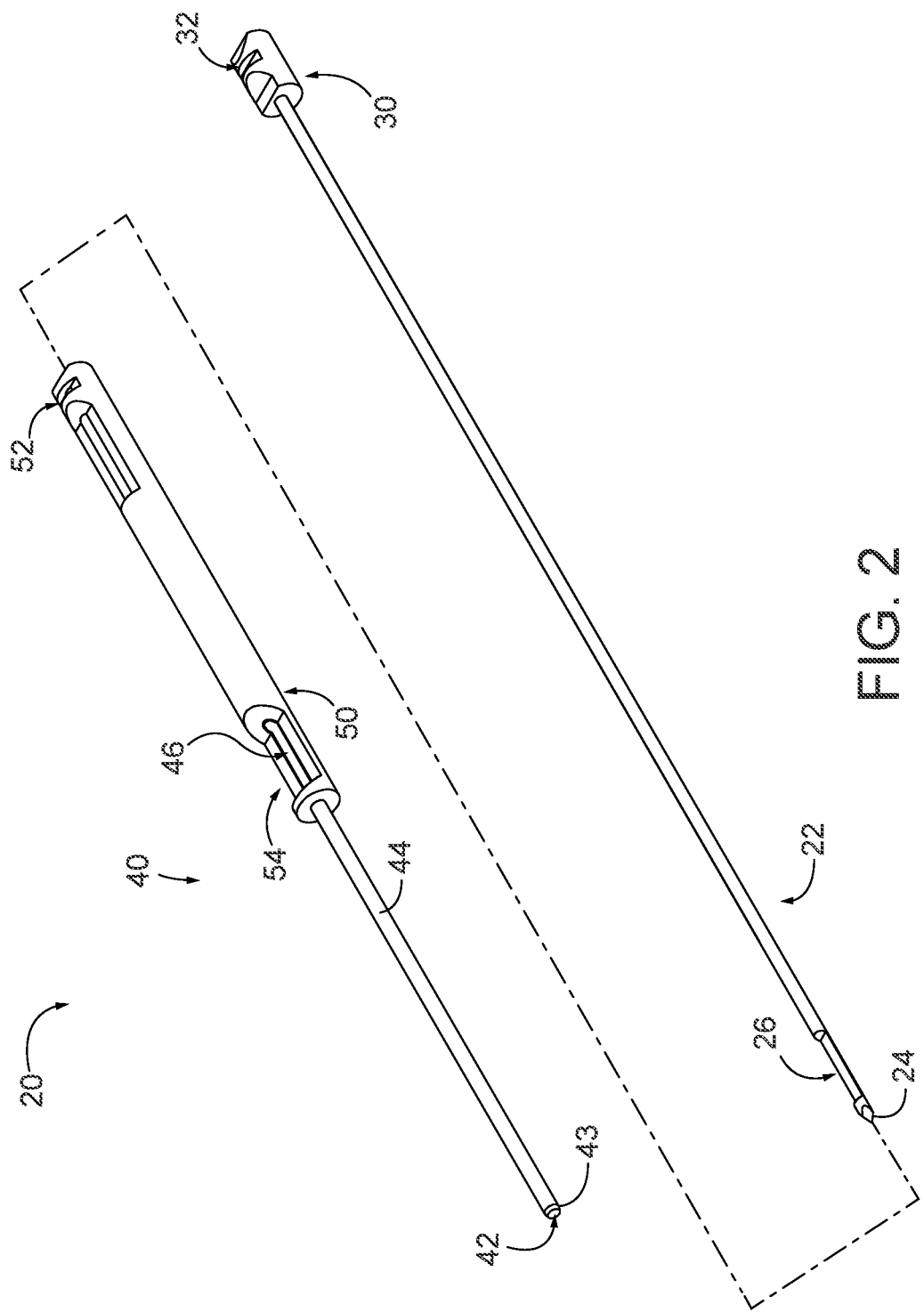
FIG. 2 depicts an exploded view of a needle assembly of the core needle biopsy device of FIG. 1.
Figure 3:
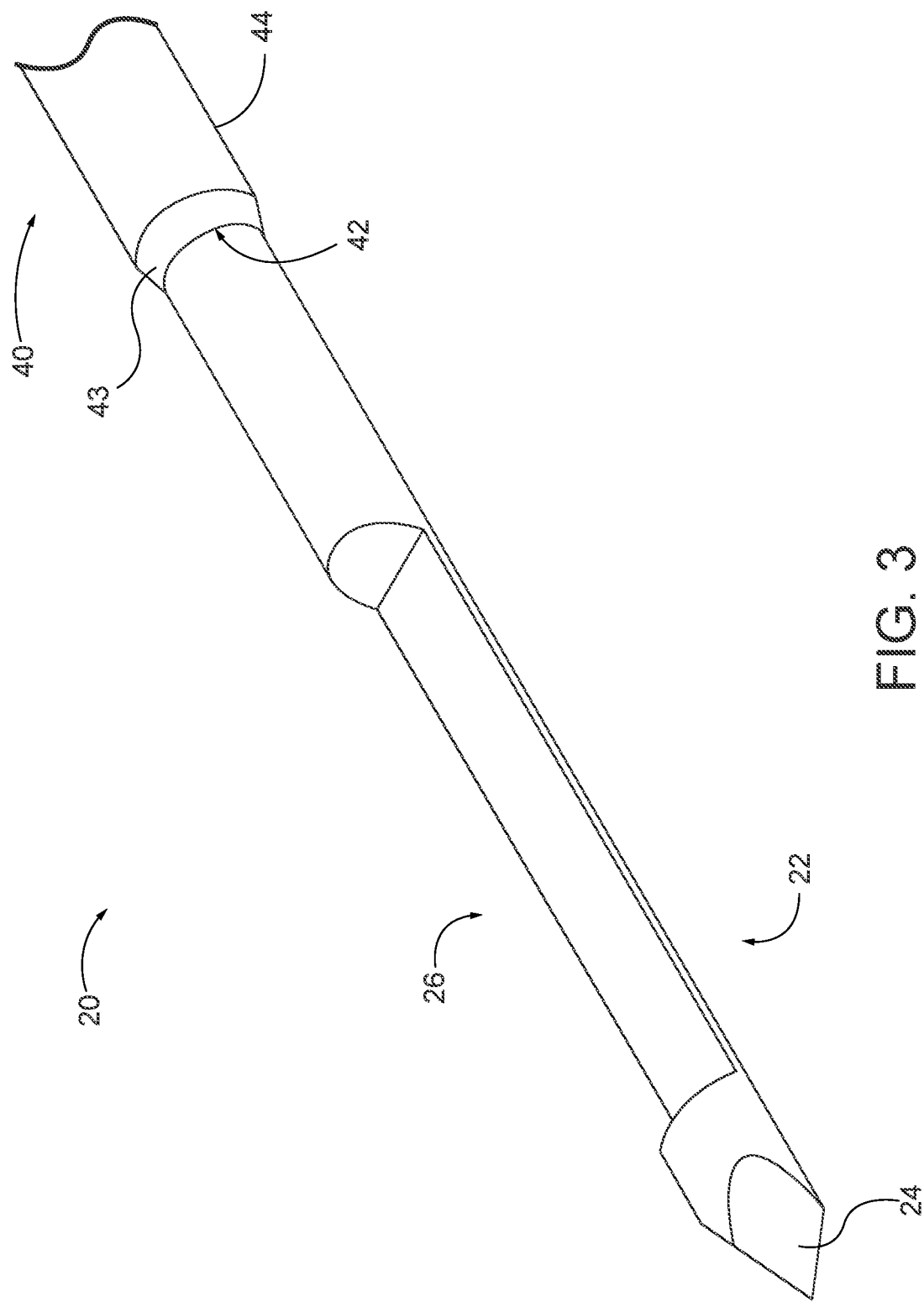
FIG. 3 depicts a perspective view of the needle assembly of FIG. 2.

FIGS. 2 and 3 show needle assembly (20) in greater detail. As can be seen in FIG. 2, needle assembly (20) comprises an elongate piercer (22) and an elongate cutter (40). As will be described in greater detail below, piercer (22) is generally movable relative to cutter (40) to pierce tissue and collect tissue samples, while cutter is generally movable relative to piercer (22) to sever tissue samples. Piercer (22) comprises a generally cylindrical rod having a sharp distal tip (24) and a notch (26) disposed adjacent to distal tip (24). As will be described in greater detail below, distal tip (24) is generally configured to penetrate tissue of a patient. As will also be described in greater detail below, notch (26) is generally configured to receive tissue therein such that a tissue sample may be collected within notch (26) after the tissue sample is severed by cutter (40).

Later in this application specific means and ways to move needle assembly (20) forward and backwards within core needle biopsy device (10) are described. At this point Applicants wish to point out that although they have included specific ways and means to move needle assembly (20) forwards and backwards, they believe, without intending to be bound thereby, that there are many alternative way to move needle assembly (20) backwards and forwards and these alternative ways should be known to people of ordinary skill in the art of designing biopsy devices.

An end portion (30) is disposed on the proximal end of piercer (22). End portion (30) of the present example is overmolded onto the proximal end of piercer (22) and is generally configured to enhance the manipulability of piercer (22). In particular, end portion (30) comprises a receiving feature (32) in the form of a lateral notch. Receiving feature (32) is configured to receive a portion of a piercer drive assembly (300). As will be described in greater detail below, this permits piercer drive assembly (300) to drive movement of piercer (22) through a predetermined sequence of movement.

Cutter (40) comprises a generally hollow cylindrical tube that is configured to receive piercer (22) therein. Cutter (40) comprises an open distal end (42), a cannula portion (44) and an end portion (50). Open distal end (42) is configured to permit at least a portion of piercer (22) to protrude from cutter (40) when piercer (22) is moved relative to cutter (40). As will be described in greater detail below, this configuration permits needle assembly (20) to move through the cutting cycle and the tissue acquisition cycle by permitting notch (26) of piercer (22) to move relative to distal end (42) of cutter (40).

Open distal end (42) of the present example includes a tapered edge (43). Tapered edge (43) is generally configured to slice through tissue to separate tissue samples when cutter (40) is moved relative to notch (26) of piercer (22). Thus, it should be understood that tapered edge (43) is generally configured to act a blade. Although the present example is described and shown as using a tapered configuration, it should be understood that in other examples various alternative configurations can be used. For instance, in some examples tapered edge (43) includes a plurality of serrations in addition or in alternative to the taper shown. In still other examples, tapered edge (43) can include any other additional or alternative cutting surface as will be apparent to those of ordinary skill in the art in view of the teachings herein.

Cannula portion (44) of cutter (40) extends proximally from distal end (42) through end portion (50) such that piercer (22) can be received with the proximal end of cutter (40). Unlike end portion (30) of piercer (22), end portion (50) of cutter (40) is generally elongate such that at least a portion of end portion (50) extends distally relative to outer housing (14). As will be described in greater detail below, this distal extension relative to outer housing (14) permits a portion of end portion (50) to be accessible to an operator for tissue sample collection purposes.

End portion (50) of cutter (40) comprises a receiving feature (52) and a tissue collection feature (54). As with receiving feature (32) of piercer (22), receiving feature (52) of end portion (50) comprises a lateral slot or other receiving feature that is configured to receive at least a portion of a cutter drive assembly (200). As will be described in greater detail below, receiving feature (52) is configured to receive at least a portion of cutter drive assembly (200) to permit cutter drive assembly (200) to move cutter (40) through a predetermined sequence of movement.

Tissue collection feature (54) is disposed distally relative to receiving feature (52). Tissue collection feature (54) generally defines an elongate notch that is open to cannula portion (44) of cutter (40). Correspondingly, cannula portion (44) includes a cutout portion (46) that is adjacent to tissue collection feature (54). Accordingly, it should be understood that tissue collection feature (54) is in communication with the hollow interior, or a lumen, defined by cannula portion (44). As will be described in greater detail below, this relationship between tissue collection feature (54) and cannula portion (44) permits an operator to remove tissue samples from cutter (40) as they are collected by piercer (22).

FIG. 3 shows piercer (22) disposed within cutter (40). As can be seen, cutter (40) is generally configured to receive piercer (22) such that piercer (22) is coaxial with cutter (40). In addition, piercer (22) is generally movable relative to open distal end (42) of cutter (40). It should be understood that in some circumstances piercer (22) moves relative to cutter (40), while cutter (40) remains stationary. In other circumstances, cutter (40) moves relative to piercer (22), while piercer (22) remains stationary. In either case, it should be understood that piercer (22) and cutter (40) are generally configured such that notch (26) of piercer (22) moves into and out of cutter (40) such that notch (26) can be disposed distally or proximally relative to open distal end (42) of cutter (40). As will be described in greater detail below, this configuration permits piercer (22) and cutter (40) to operate cooperatively to pierce tissue, cut a tissue sample, and retract the tissue sample for collection by an operator via tissue collection feature (54).

Figure 4:
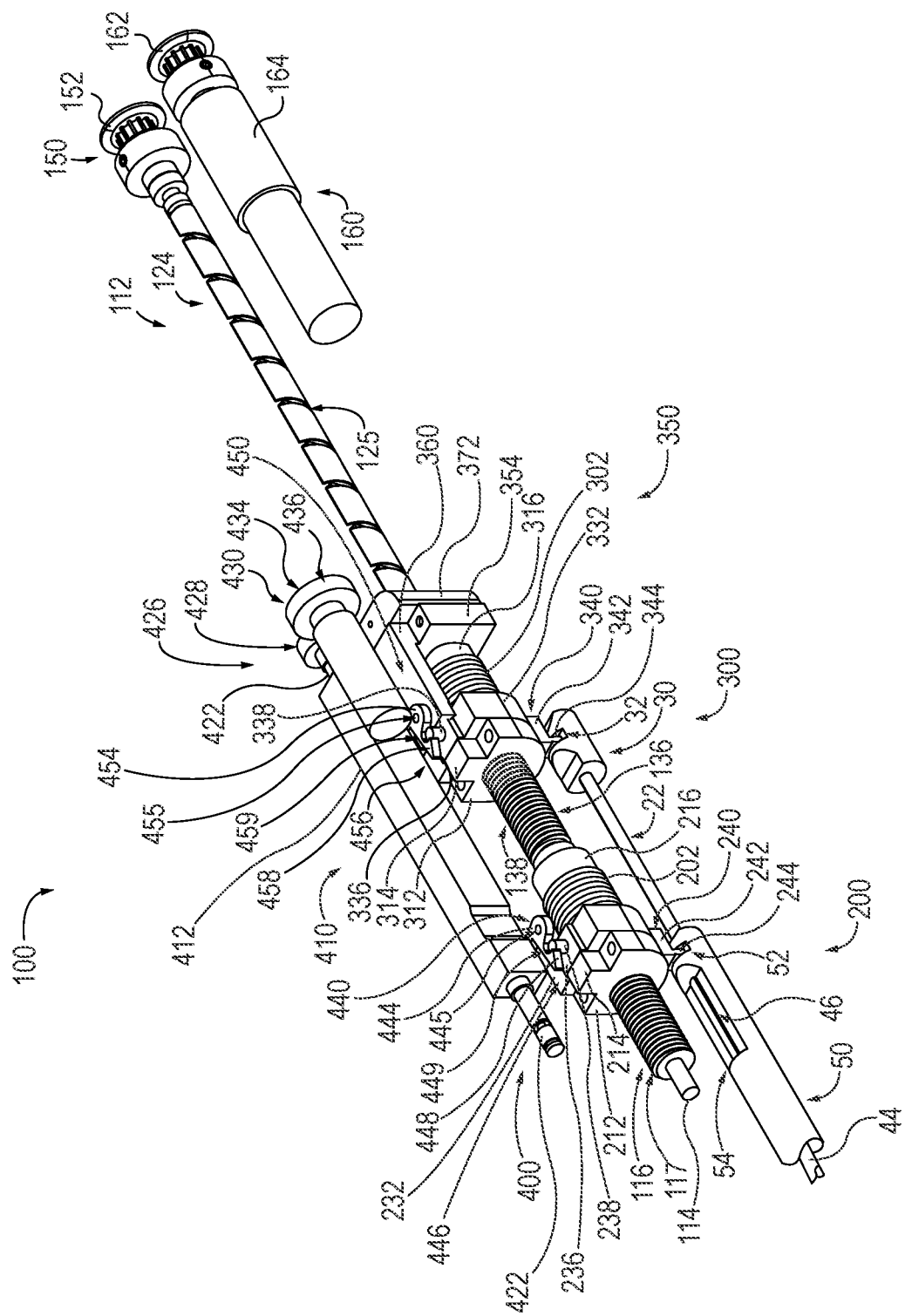
FIG. 4 depicts a perspective view of a drive assembly of the core needle biopsy device of FIG. 1.
Figure 5:
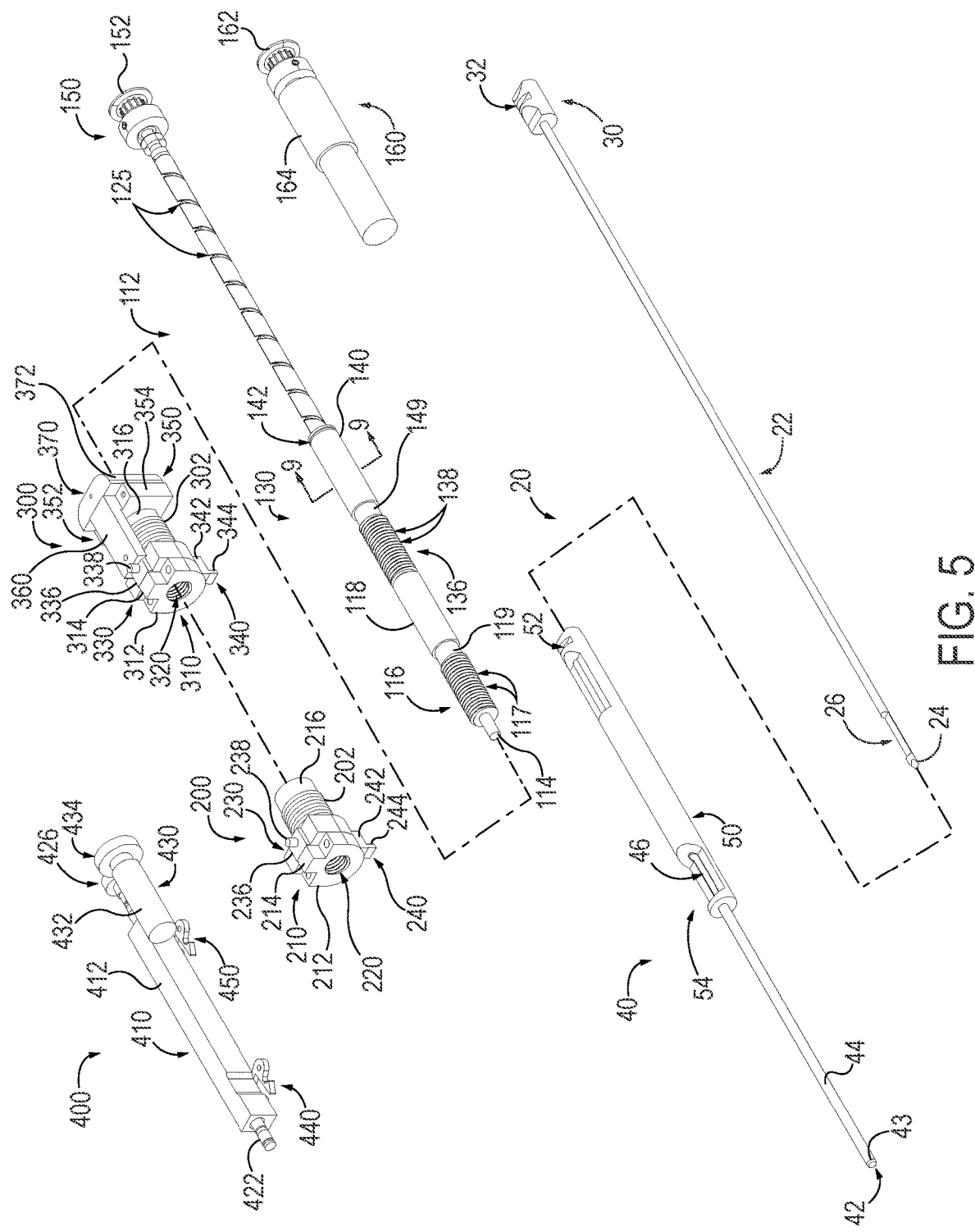
FIG. 5 depicts an exploded view of the drive assembly of FIG. 4.
Figure 6:
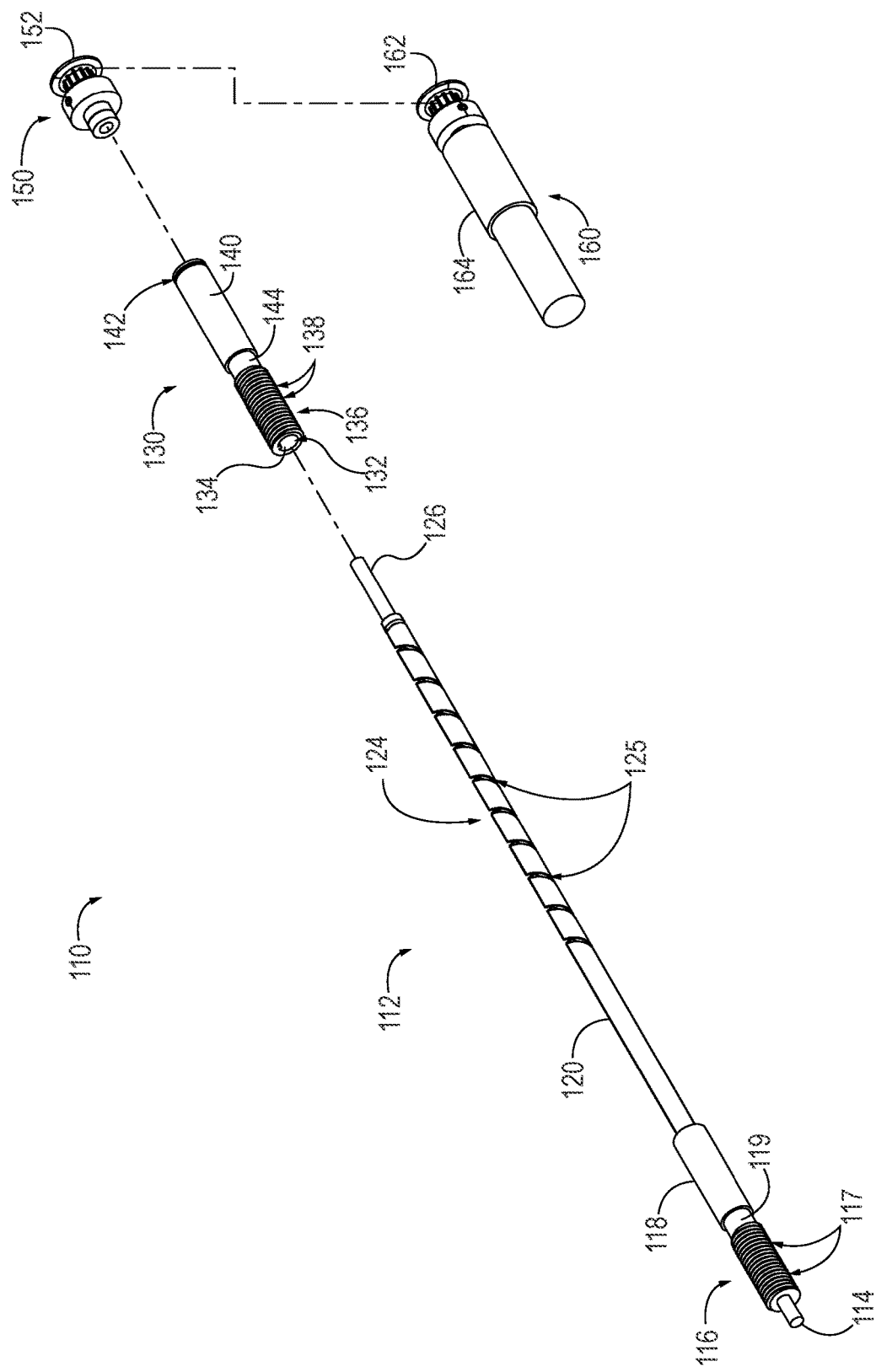
FIG. 6 depicts an exploded view of a needle cocking assembly of the drive assembly of FIG. 4.

FIGS. 4 and 5 show the internal components of body (12) of biopsy device (10) with outer housing (14) removed. As can be seen, inside outer housing (14), body (12) includes a drive assembly (100). Drive assembly (100) is generally configured to engage needle assembly (20) to drive piercer (22) and cutter (40) through a predetermined sequence of movements to thereby pierce tissue and acquire a plurality of tissue samples with a single insertion of needle assembly (20) into a patient. Although not shown, it should be understood that outer housing (14) defines various internal geometries that support or otherwise engage drive assembly (100). As will be understood, such internal geometries are used to provide relative movement of various components of drive assembly (100) relative to other components of drive assembly (100) and/or outer housing (14).

Drive assembly (100) comprises a needle cocking assembly (110), a cutter drive assembly (200), a piercer drive assembly (300), and a release assembly (400). Generally, and as will be described in greater detail below, needle cocking assembly (110) engages cutter drive assembly (200) and piercer drive assembly (300) to cock cutter drive assembly (200) and piercer drive assembly (300), which correspondingly cock cutter (40) and piercer (22). Release assembly (400) also engages cutter drive assembly (200) and piercer drive assembly (300) to selectively release and fire cutter drive assembly (200) and piercer drive assembly (300) to thereby selectively release and fire cutter (40) and piercer (22).

Figure 7:
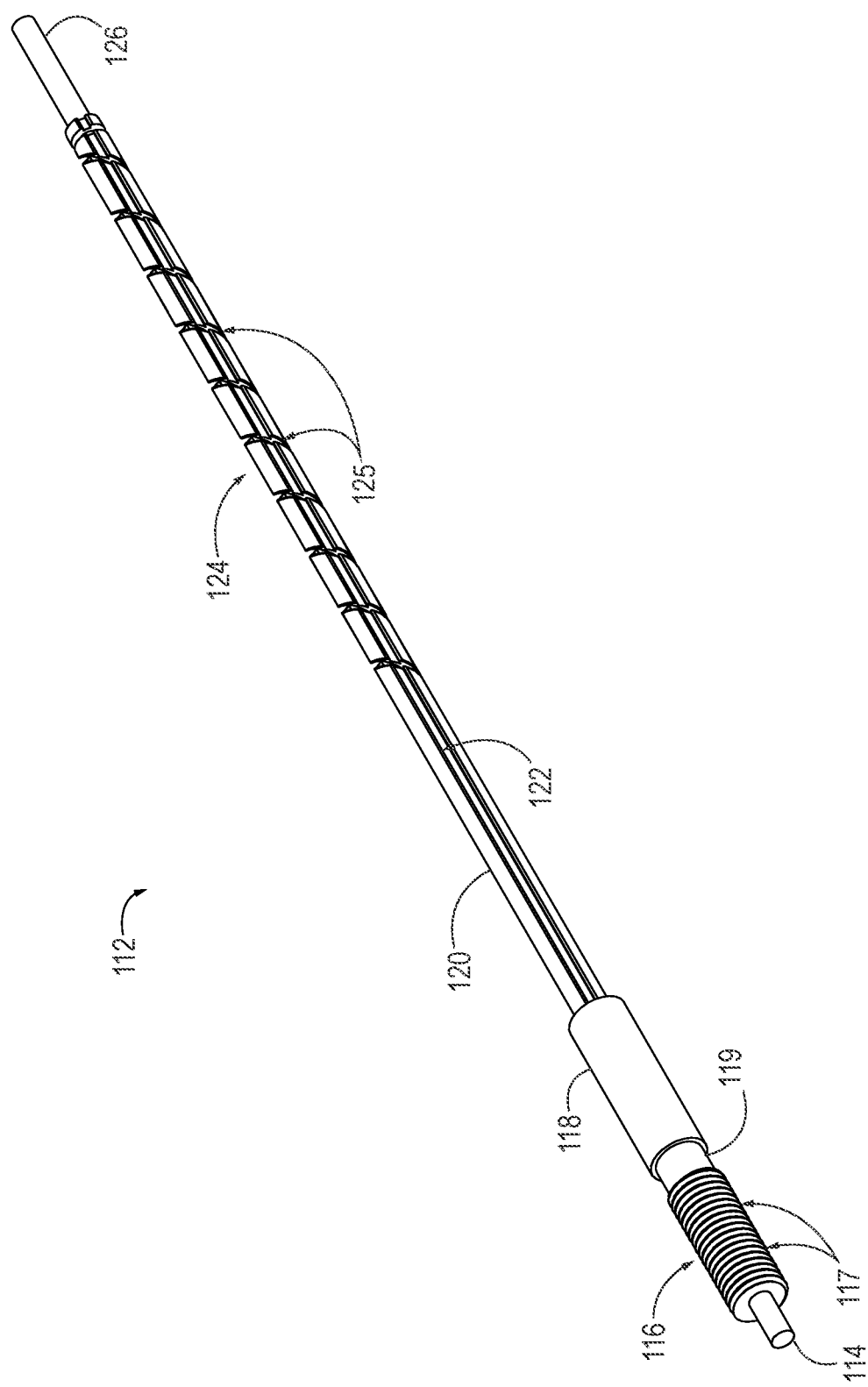
FIG. 7 depicts a perspective view of a lead screw of the needle cocking assembly of FIG. 6.

Needle cocking assembly (110) is best seen in FIGS. 6-9. As can be seen, needle cocking assembly (110) comprises a lead screw (112), a carriage nut (130), a drive member (150), and a motor assembly (160). Lead screw (112) is best seen in FIG. 7. As can be seen lead screw (112) is generally an elongate multi-threaded rod. Lead screw (112) comprises a distal end (114), first threaded portion (116), a slide stop portion (118), a non-threaded portion (120), a keyway (122), a second threaded portion (124), and a proximal end (126).

Distal end (114) of lead screw (112) generally comprises a cylindrical shape extending distally from first threaded portion (116). Distal end (114) is configured to be received by at least a portion of outer housing (14) or another intermediate connecting member, such as a bearing, to permit lead screw (112) to rotate about a fixed axis. Thus, it should be understood that distal end (114) generally acts as a boss or locating feature to permit rotation of lead screw (112).

First threaded portion (116) is disposed proximally of distal end (114). First threaded portion (116) includes threads (117) which have a relatively fine pitch. As will be described in greater detail below, threads (117) are generally configured to engage a portion of cutter drive assembly (200) to convert rotational motion of lead screw (112) into translation of at least a portion of cutter drive assembly (200). This conversion of motion generally results in proximal and distal translation of at least a portion of cutter drive assembly (200), which results in cocking of cutter drive assembly (200).

Slide stop portion (118) is disposed proximally of first threaded portion (116) and distally of keyway (122), second threaded portion (124) and proximal end (126). Slide stop portion (118) comprises a generally cylindrical shape. The diameter of slide stop portion (118) generally corresponds to the major pitch diameter of first threaded portion (116). As will be described in greater detail below, these size and shape characteristics of slide stop portion (118) permit slide stop portion (118) to provide coaxial support of at least a portion of cutter drive assembly (200) as cutter drive assembly (200) moves relative to lead screw (112).

The diameter of slide stop portion (118) is also generally greater than the diameter of non-threaded portion (120) of lead screw (112). As will be understood, this differential in diameter between slide stop portion (118) and non-threaded portion (120) permits slide stop portion (118) to act as a mechanical stop feature. As will be described in greater detail below, this mechanical stop feature is configured to limit distal translation of carriage nut (130) as carriage nut (130) moves along lead screw (112).

Between slide stop portion (118) and first threaded portion (116), lead screw (112) defines an indented portion (119). As will be described in greater detail below, indented portion (119) is generally configured to permit a portion of cutter drive assembly (200) to "free-wheel" when cutter drive assembly (200) is disposed in axial alignment with indented portion (119). It should be understood that the term "free-wheel" used herein refers to the ability of lead screw (112) to continue to rotate without additional proximal translation of cutter drive assembly (200) and without binging between lead screw (112) and at least a portion of cutter drive assembly (200). It should be understood that during free-wheeling, at least a portion of cutter drive assembly (200) is generally disengaged from first threaded portion (116) of lead screw (112). However, it should be understood that the length of indented portion (119) is sufficiently limited such that when rotation of lead screw (112) is reversed, at least a portion of cutter drive assembly (200) reengages with first threaded portion (116) of lead screw (112). Further details of the relationship between indented portion (119), first threaded portion (116) and cutter drive assembly (200) will be described in greater detail below.

As shown in FIG. 7, non-threaded portion (120) is proximally adjacent to slide stop portion (118). Non-threaded portion (120) is also distally adjacent to second threaded portion (124) and is disposed distally of proximal end (126). Non-threaded portion (120) is generally of a cylindrical shape without threads or other features. However, as can be seen in FIG. 7, keyway (122) extends through non-threaded portion (120) and through second threaded portion (124). As previously described above with respect to slide stop portion (118), non-threaded portion (120) has a diameter that is generally less than the diameter defined by slide stop portion (118). As also described above, this differential in diameter between non-threaded portion (120) and slide stop portion (118) permits non-threaded portion (120) to provide a mechanical stop feature for carriage nut (130), as will be described in greater detail below.

Second threaded portion (124) is disposed between non-threaded portion (120) and proximal end (126), with non-threaded portion (120) distal of second threaded portion (124) and proximal end (126) proximal of non-threaded portion (120). Second threaded portion (124) includes a plurality of relatively course threads (125). Threads (125) are generally course relative to threads (117) of first threaded portion (116). Thus it should be understood that with both threads (125, 117) acting to transfer rotary movement into axial translation, threads (125) of second threaded portion (124) will generally provide faster translation from the same rotary input relative to threads (117) of first threaded portion (116).

Second threaded portion (124) of the present example is configured to engage at least a portion of piercer drive assembly (300). As will be described in greater detail below, threads (125) of second threaded portion (124) are generally configured to convert rotatory motion of lead screw (112) into axial translation of at least a portion of piercer drive assembly (300). This conversion of rotary motion into translation permits piercer drive assembly to translate piercer (22) for the purpose of tissue collection via tissue collection feature (54).

In the present example, second threaded portion (124) and non-threaded portion (120) are arranged such that non-threaded portion (120) defines a length. The length of non-threaded portion (120) is generally just greater than the approximate length of carriage nut (130). As will be understood, the length of non-threaded portion permits carriage nut (130) to be axially translated by piercer drive assembly (300) until being stopped by slide stop portion (120). Once translation is ceased by slide stop portion (120), however, non-threaded portion (120) permits lead screw (112) to "free-wheel" relative to piercer drive assembly (300). It should be understood that the term "free-wheel" used herein refers to the ability of lead screw (112) to continue to rotate without additional translation of piercer drive assembly (300) and without binding between lead screw (112) and piercer drive assembly (300). During free-wheeling, piercer drive assembly (300) generally disengaged from second threaded portion (124). However, it should be understood that the length of non-threaded portion remains limited to an extent such that when rotation of lead screw (112) is reversed, piercer drive assembly (300) reengages with second threaded portion (124). Further details of the relationship between non-threaded portion (120), second threaded portion (124) and piercer drive assembly (300) will be described in greater detail below.

Returning to FIG. 6, rotation of lead screw (112) is provided by drive member (150) and motor assembly (160). In particular, drive member (150) of the present example is configured to be fixedly secured to proximal end (126) of lead screw (112). Drive member (150) includes a rotary communication feature (152) which is configured to transmit rotary motion from a rotary communication feature (162) of motor assembly (160) to lead screw (112). In the present example, rotary communication features (152, 162) are configured as belt drives such that rotatory motion is communicated via a belt (not shown). It should be understood that although rotary communication features (152, 162) are shown as using a belt drive, any other suitable rotary communication feature may be used. For instance, in some examples rotary communication features (152, 162) can include one or more gears with varying gear ratios to communicate rotary motion from motor assembly (160) to lead screw (112). Of course, in other examples, rotary communication features (152, 162) can be omitted entirely such that motor assembly (160) includes a direct drive that directly communicates rotary motion to lead screw (112).

As described above, motor assembly (160) includes a rotary communication feature (162). Additionally, motor assembly (160) includes a rotary power source (164). Rotary power source (164) of the present example includes an electric motor. In other examples, rotary power source (164) may include any other suitable power source such as a pneumatic motor, a piezo electric motor, and/or etc.

Figure 8:
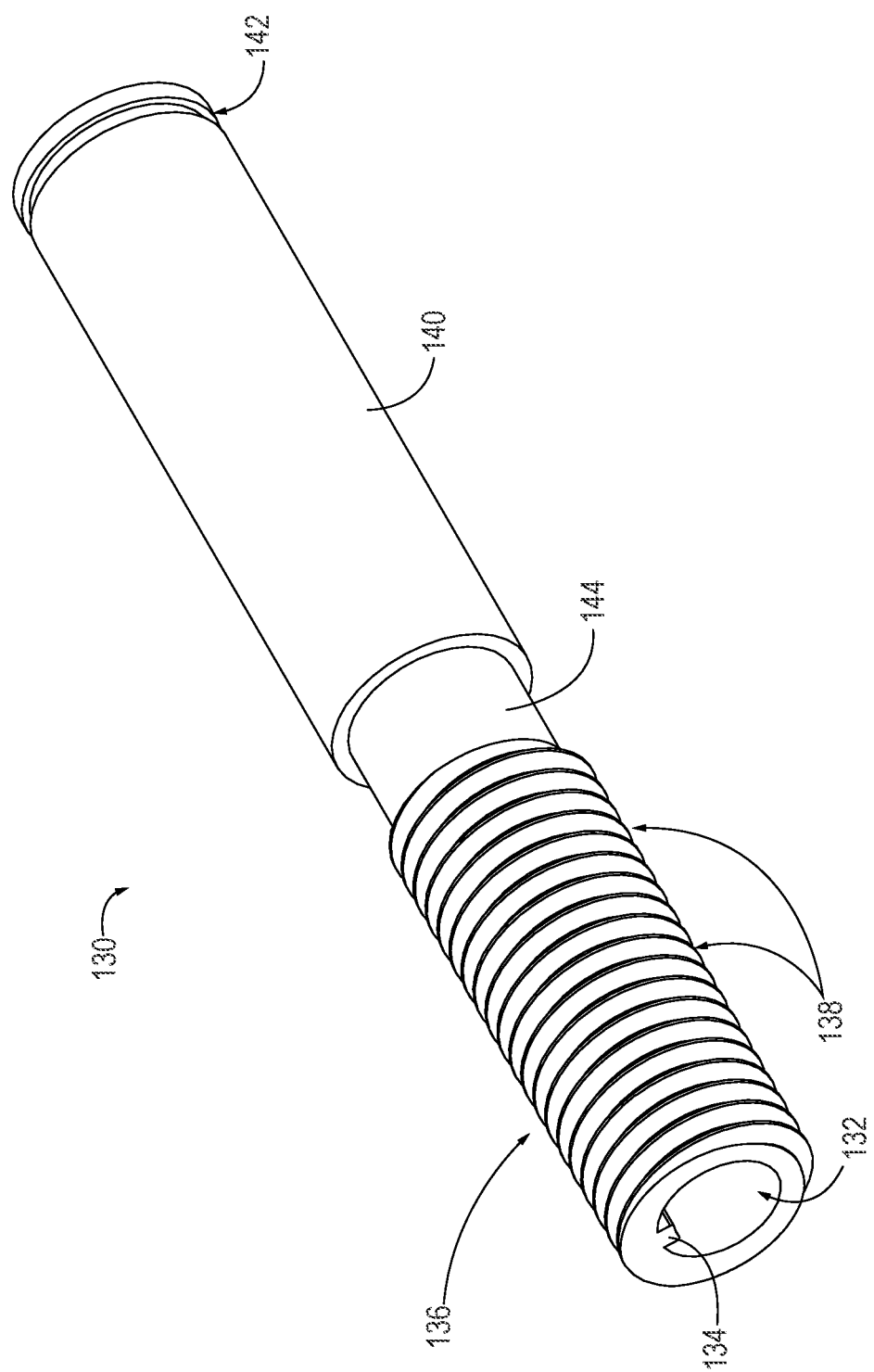
FIG. 8 depicts a perspective view of a carriage nut of the needle cocking assembly of FIG. 6.

FIG. 8 shows carriage nut (130) in greater detail. As can be seen, carriage nut (130) comprises a generally cylindrical shape with a bore (132) extending entirely therethough. Extending inwardly into bore (132) is a key (134). Key (134) extends axially through at least a portion of the length of carriage nut (130). As will be described in greater detail below, key (134) is generally configured to engage keyway (122) of lead screw (112) such that carriage nut (130) is generally configured to rotate in conjunction with lead screw (112).

On the exterior of carriage nut (130), carriage nut (130) defines a threaded portion (136) and a slide portion (140). Threaded portion (136) includes a plurality of threads (138). Threads (138) generally include a pitch that is relatively fine and generally equivalent to the pitch of threads (117) of first threaded portion (116) described above with respect to lead screw (112). As will be described in greater detail, threads (138) of threaded portion (136) are generally configured to engage at least a portion of piercer drive assembly (300) to move at least a portion of piercer drive assembly (300) thorough a variety of positions to thereby cock and fire piercer (22).

Slide portion (140) defines a generally cylindrical shape having an outer diameter. The outer diameter of slide portion (140) approximately corresponds to the major diameter of threaded portion (136). As will be described in greater detail below, this correspondence in diameters permits at least a portion of cutter drive assembly (200) to freely slide over both slide portion (140) and threaded portion (136), while remaining generally coaxial with carriage nut (130).

Adjacent to the proximal end of carriage nut (130), slide portion (140) defines an annular channel (142). As will be described in greater detail below, annular channel (142) is configured to receive at least a portion of piercer drive assembly (300) to axially secure at least a portion of piercer drive assembly (300) to carriage nut (130). However, as will also be described in greater detail below, any portion of cutter drive assembly (300) axially secured to carriage nut (130) via cannula channel (142) is rotatably unsecured such that carriage nut (130) can rotate relative to piercer drive assembly (300).

Disposed between slide portion (140) and threaded portion (136), carriage nut (130) defines an indented portion (144). Indented portion (144) is defined by an outer diameter that is generally less than the major diameter of threaded portion (136) and the outer diameter of slide portion (140). In addition, indented portion (144) defines a length. As will be described in greater detail below, the length of indented portion (144) is generally approximately equivalent to at least a portion of piercer drive assembly (300) to permit a portion of piercer drive assembly (300) to free-wheel relative to carriage nut (130).

As will be described in greater detail below, indented portion (144) is generally configured to permit a portion of piercer drive assembly (300) to free-wheel when piercer drive assembly (300) is disposed in axial alignment with indented portion (144). As similarly discussed above with respect to non-threaded portion (120) of lead screw (112), the term "free-wheel" used herein refers to the ability of carriage nut (130) to continue to rotate without additional proximal translation of piercer drive assembly (300) and without binging between carriage nut (130) and at least a portion of piercer drive assembly (300). It should be understood that during free-wheeling, at least a portion of piercer drive assembly (300) is generally disengaged from threaded portion (136) of carriage nut (130). However, it should be understood that the length of indent portion (144) is sufficiently limited such that when rotation of carriage nut (130) is reversed, at least a portion of piercer drive assembly (300) reengages with threaded portion (136) of carriage nut (130). Further details of the relationship between indented portion (144), threaded portion (136) and piercer drive assembly (300) will be described in greater detail below.

Figure 9:
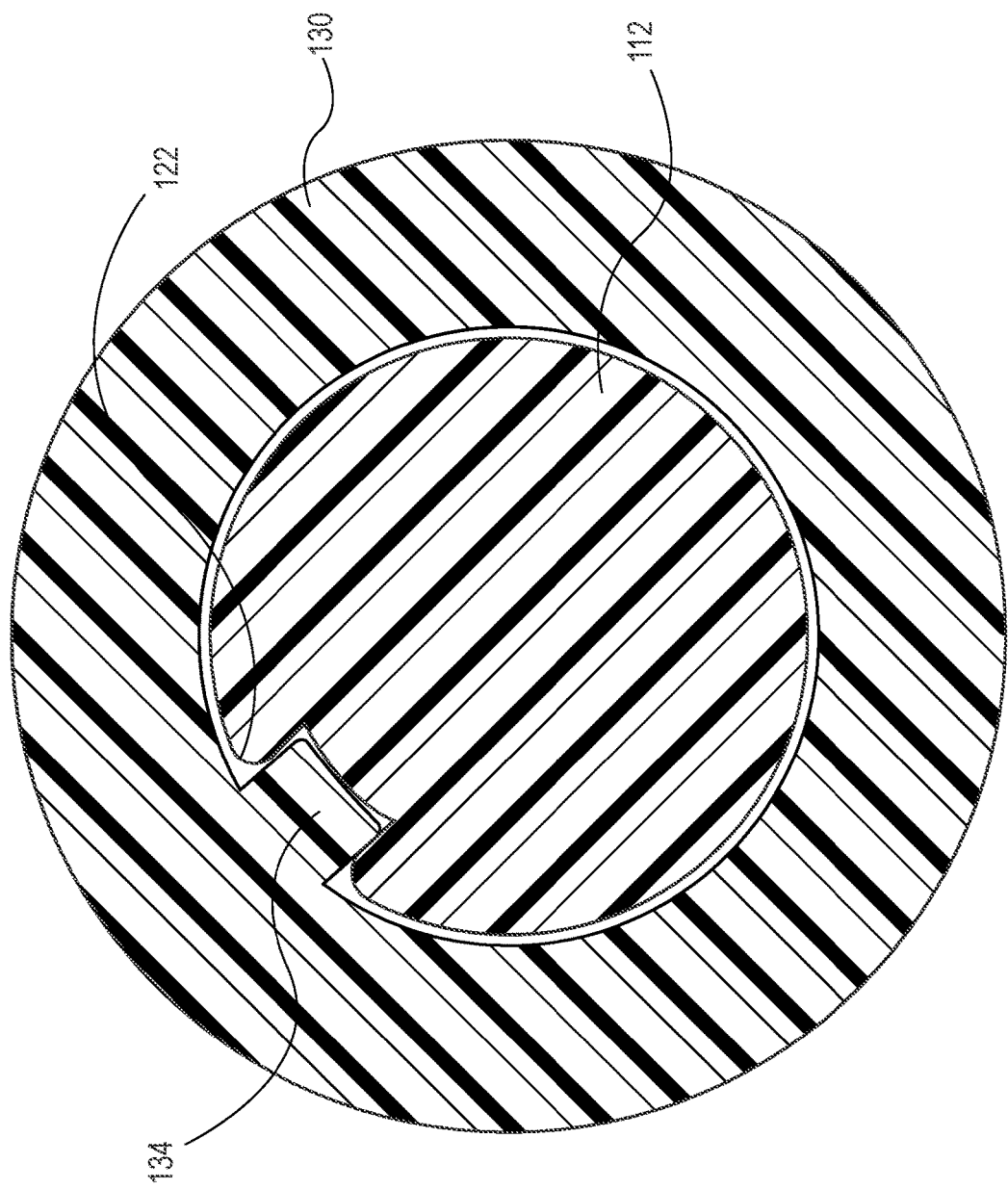
FIG. 9 depicts a side cross-sectional view of the needle cocking assembly of FIG. 6, the cross-section taken along line 9-9 of FIG. 5.

FIG. 9 shows carriage nut (130) coaxially disposed on lead screw (112). As can be seen, when carriage nut (130) is disposed on lead screw (112), key (134) extends into keyway (122) of lead screw (112). Accordingly, it should be understood that keyway (122) of lead screw (112) is configured to engage key (134) such that rotation of lead screw (112) results in corresponding rotation of carriage nut (130). It should be understood that since keyway (122) extends through both second threaded portion (124) and non-threaded portion (120) of lead screw (112), keyway (122) is configured to engage key (134) of carriage nut (130) as carriage nut (130) travels axially about second threaded portion (124) and non-threaded portion (120) of lead screw (112).

FIG. 10A shows cutter actuation assembly (200) in greater detail. In particular, cutter actuation assembly (200)

comprises a cocking member (210), an actuation member (230), and a resilient member (202). Cocking member (210) comprises a stop portion (212), a slide portion (216), and a bore (220) extending axially though cocking member (210). Stop portion (212) is generally configured to act as a mechanical stop for actuation member (230). Accordingly, stop portion (212) forms a shape that is similar to a partially cylindrical flange or another similar feature. As will be described in greater detail below, this mechanical stop feature of stop portion (212) is generally configured to manipulate motion of actuation member (230) as actuation member (230) moves cutter (40) through a predetermined sequence of motion.

Stop portion (212) further defines an alignment tab (214) extending upwardly relative to bore (220). Alignment tab (214) comprises a generally rectangular or cubic shape. In other examples, alignment tab (214) may comprise any other suitable shape such as cylindrical, ball-shaped, triangular, and/or etc. Although not shown, it should be understood that alignment tab (214) is configured to be received within a corresponding channel or track disposed within outer housing (14) or an intermediate housing (not shown). Such a channel or track is configured to restrict motion of cocking member (210) to a particular predetermined axial path. Such a channel or track is further configured to prevent rotation of cocking member (210) relative to lead screw (112) to thereby permit lead screw (112) to drive axial motion of cocking member (210), as will be described in greater detail below.

Slide portion (216) of cocking member (210) extends proximally from stop portion (212). Slide portion (216) comprises a generally cylindrical outer surface that is configures to receive actuation member (230). As will be described in greater detail below, actuation member (230) is generally coaxially slidable on slide portion (216) to actuate cutter (40) through a predetermined sequence of motion. However, slide portion (216) has a diameter that is less than the size or diameter of stop portion (212). Accordingly, it should be understood that actuation member (230) is generally coaxially slidable on slide portion (216) until actuation member (230) reaches stop portion (212). At which point, any additional distal sliding relative to slide portion (216) is ceased by stop portion (212).

As described above, bore (220) of cocking member (210) extends through both stop portion (212) and slide portion (216). Bore (220) defines a plurality of threads (222) extending inwardly into bore (220). As best seen in FIG. 10B, threads (222) of bore (220) extend through only the length of bore (220) corresponding to the length of stop portion (212). Although threads (222) of the present example only extend partially though bore (220), it should be understood that in other examples threads (222) can extend for the entire length of bore (220). However, it should be understood that in such examples certain complementary features of lead screw (112) may require adjustment in length/size to accommodate the additional length of threads (222).

Bore (220) is configured to receive at least a portion of lead screw (112). In particular, bore (220) is configured to receive first threaded portion (116), indented portion (119), and/or slide stop portion (118) of lead screw (112) at various stages during the cutting cycle and the tissue acquisition cycle, as will be described in greater detail below. As will be understood, threads (222) are configured to engage threads (117) of first threaded portion (116). Thus, it should be understood that rotation of lead screw (112) relative to cocking member (210) will generally result in axial translation of cocking member (210) relative to lead screw (112).

As described above, threads (222) of bore (220) are generally limited to the length of stop portion (212). Because a portion of bore (220) in the present example is un-threaded (e.g., the portion corresponding to slide portion (216)), it should be understood that bore (220) can receive at least a portion of slide stop portion (118) of lead screw (112). However, because slide stop portion (118) defines a diameter approximately equivalent to the major diameter of first threaded portion (116) of lead screw (112), it should be understood that as cocking member (210) moves proximally relative to lead screw (112) such relative motion will only be permitted until threads (222) reach slide stop portion (118) of lead screw (112). Once threads (222) reach slide stop portion (118) of lead screw (112), an interference between the major diameter of threads (222) and the outer diameter of slide stop portion (118) will prevent further proximal movement of cocking member (210). Moreover, threads (222) at this stage will be adjacent to intended portion (119) and therefore disengaged with threads (117) of first threaded portion (116).

Actuation member (230) comprises a body (232), an alignment tab (236), and an actuation tab (240). Body (232) comprises a shape that is generally similar to stop portion (212) described above with respect to cocking member (210). Like with stop portion (212), body (232) defines a bore (234) extending through body (232). Bore (234) of body (232) is configured to receive slide portion (216) of cocking member (210). Thus, it should be understood that actuation member (230) is generally coaxially slidable with slide portion (216) of cocking member (210).

Alignment tab (236) extends upwardly from body (232). Like with alignment tab (214) of cocking member (210), alignment tab (236) of actuation member (230) is configured to engage a channel or track disposed in outer housing (14) or an intermediate housing (not shown). As similarly discussed above, this configuration generally permits such a channel or tack to restrict the motion of actuation member (230) to a predetermined path. However, unlike alignment tab (214) discussed above, alignment tab (236) of actuation member (230) only extends for a relatively small distance from body (232). Instead of alignment tab (236) extending for the full extent as seen with alignment tab (214), a portion of alignment tab (236) of actuation member (230) is replaced with a release member (238). Release member (238) comprises a generally cylindrical shape. As will be described in greater detail below, release member (238) is generally configured to be received by release assembly (400) to temporarily hold actuation member (230) in a cocked position and then selectively release actuation member (230) via actuation of release assembly (400).

Actuation tab (240) extends downwardly from body (232). Actuation tab (240) comprises an upper portion (242) and a lower portion (244). Upper portion (242) comprises a generally rectangular shape. Although not shown, it should be understood that in some examples upper portion (242) can be configured to be received within a cannel or track of outer housing (14) or an intermediate internal housing (not shown) thereof. In such examples, upper portion (242) functions to restrict motion of actuation member (230) to a predetermined path.

Lower portion (244) of actuation tab (240) extends downwardly from upper portion (242). Lower portion (244) is generally configured to be received within receiving feature (52) of cutter (40). As will be described in greater detail below, when lower portion (244) is received within receiving feature (52) of cutter (40), actuation member (230) is generally permitted to drive cutter (40) through a predetermined sequence of movements via lower portion (244). Although not show, it should be understood that in examples where upper portion (242) is received within a channel or track of outer housing (14) or an intermediate internal housing, such a channel or track may include an opening or additional channel to prevent lower portion (244) to extend through such a channel or track to receiving feature (52) of cutter (40).

When cutter drive assembly (200) is assembled (e.g., as seen in FIG. 4), spring (202) is disposed adjacent to the proximal end of actuation member (230). In addition, spring (202) is disposed coaxially around slide portion (216) of cocking member (210) and/or coaxially around slide stop portion (118) of lead screw (112), depending on the particular stage of operation of drive assembly (100). As will be described in greater detail below, spring (202) is generally configured to drive actuation member (230) distally after actuation member (230) is released by release assembly (400). Spring (202) generally defines an outer diameter that approximately corresponds to the outer diameter of slide portion (216) of cocking member (210). Although spring (202) of the present example is shown as a coil spring, it should be understood that any other suitable resilient member may be used as will be apparent to those of ordinary skill in the art in view of the teachings herein.

FIG. 11A shows piercer drive assembly (300) in greater detail. As can be seen, piercer drive assembly (300) comprises a cocking member (310), an actuation member (330), a piercer retraction assembly (350), and a spring (302). Cocking member (310) of piercer drive assembly (300) is similar to cocking member (210) of cutter drive assembly (200). In particular, like with cocking member (210), cocking member (310) comprises a stop portion (312), a slide portion (316), and a bore (320) extending axially though cocking member (310). Stop portion (312) is generally configured to act as a mechanical stop for actuation member (330). Accordingly, stop portion (312) forms a shape that is similar to a partially cylindrical flange or another similar feature. As will be described in greater detail below, this mechanical stop feature of stop portion (312) is generally configured to manipulate motion of actuation member (330) as actuation member (330) moves piercer (22) through a predetermined sequence of motion.

Stop portion (312) further defines an alignment tab (314) extending upwardly relative to bore (320). Alignment tab (314) comprises a generally rectangular or cubic shape. In other examples, alignment tab (314) may comprise any other suitable shape such as cylindrical, ball-shaped, triangular, and/or etc. Although not shown, it should be understood that alignment tab (314) is configured to be received within a corresponding channel or track disposed within outer housing (14) or an intermediate housing (not shown). Such a channel or track is configured to restrict motion of cocking member (310) to a particular predetermined axial path. Such a channel or track is further configured to prevent rotation of cocking member (310) relative to lead screw (112) and carriage nut (130) to thereby permit lead screw (112) and carriage nut (130) to drive axial motion of cocking member (310), as will be described in greater detail below.

Slide portion (316) of cocking member (310) extends proximally from stop portion (312). Slide portion (316) comprises a generally cylindrical outer surface that is configures to receive actuation member (330). As will be described in greater detail below, actuation member (330) is generally coaxially slidable on slide portion (316) to actuate cutter (40) through a predetermined sequence of motion. However, slide portion (316) has a diameter that is less than the size or diameter of stop portion (312). Accordingly, it should be understood that actuation member (330) is generally coaxially slidable on slide portion (316) until actuation member (330) reaches stop portion (312). At which point, any additional distal sliding relative to slide portion (316) is ceased by stop portion (312).

As described above, bore (320) of cocking member (310) extends through both stop portion (312) and slide portion (316). Bore (320) defines a plurality of threads (322) extending inwardly into bore (320). As can best be seen in FIG. 11B, threads (322) of bore (320) extend through only the longitudinal length of bore (320) corresponding to the length of stop portion (312). In other examples, threads (322) can alternatively extend for the entire length of bore (320). However, it should be understood that in such examples certain complementary features of carriage nut (130) may require adjustment in length/size to accommodate the additional length of threads (322).

Bore (320) is configured to receive at least a portion of carriage nut (130). In particular, bore (320) is configured to receive threaded portion (136), indented portion (144), and/or slide portion (140) of carriage nut (130) at various stages during the cutting cycle and the tissue acquisition cycle, as will be described in greater detail below. As will be understood, threads (322) are configured to engage threads (138) of threaded portion (136) of carriage nut (130). Thus, it should be understood that rotation of carriage nut (130) via lead screw (112) relative to cocking member (310) will generally result in axial translation of cocking member (310) relative to carriage nut (130) and lead screw (112).

As described above, threads (322) of bore (320) are generally limited to the length of stop portion (312). Because a portion of bore (320) in the present example is un-threaded (e.g., the portion corresponding to slide portion (316)), it should be understood that bore (320) can receive at least a portion of slide portion (140) of carriage nut (130). However, because slide portion (140) defines a diameter approximately equivalent to the major diameter of threaded portion (136) of carriage nut (130), it should be understood that as cocking member (310) moves proximally relative to carriage nut (130) and lead screw (112) such relative motion will only be permitted until threads (322) reach slide portion (140) of carriage nut (130). Once threads (322) reach slide portion (140) of carriage nut (130), an interference between the major diameter of threads (322) and the outer diameter of slide portion (140) will prevent further proximal movement of cocking member (310). Moreover, threads (322) at this stage will be adjacent to intended portion (144) and therefore disengaged with threads (138) of threaded portion (136).

Actuation member (330) comprises a body (332), an alignment tab (336), and an actuation tab (340). Body (332) comprises a shape that is generally similar to stop portion (312) described above with respect to cocking member (310). Like with stop portion (312), body (332) defines a bore (334) extending through body (332). Bore (334) of body (332) is configured to receive slide portion (316) of cocking member (310). Thus, it should be understood that actuation member (330) is generally coaxially slidable with slide portion (316) of cocking member (310).

Alignment tab (336) extends upwardly from body (332). Like with alignment tab (314) of cocking member (310), alignment tab (336) of actuation member (330) is configured to engage a channel or track disposed in outer housing (14) or an intermediate housing (not shown). As similarly discussed above, this configuration generally permits such a channel or tack to restrict the motion of actuation member (330) to a predetermined path. However, unlike alignment tab (314) discussed above, alignment tab (336) of actuation member (330) only extends for a relatively small distance from body (332). Instead of alignment tab (336) extending for the full extent as seen with alignment tab (314), a portion of alignment tab (336) of actuation member (330) is replaced with a release member (338). Release member (338) comprises a generally cylindrical shape. As will be described in greater detail below, release member (338) is generally configured to be received by release assembly (400) to temporarily hold actuation member (330) in a cocked position and then selectively release actuation member (330) via actuation of release assembly (400).

Actuation tab (340) extends downwardly from body (332). Actuation tab (340) comprises an upper portion (342) and a lower portion (344). Upper portion (342) comprises a generally rectangular shape. Although not shown, it should be understood that in some examples upper portion (342) can be configured to be received within a cannel or track of outer housing (14) or an intermediate internal housing (not shown) thereof. In such examples, upper portion (342) functions to restrict motion of actuation member (330) to a predetermined path.

Lower portion (344) of actuation tab (340) extends downwardly from upper portion (342). Lower portion (344) is generally configured to be received within receiving feature (32) of piercer (22). As will be described in greater detail below, when lower portion (344) is received within receiving feature (32) of piercer (22), actuation member (330) is generally permitted to drive piercer (22) through a predetermined sequence of movements via lower portion (344). Although not show, it should be understood that in examples where upper portion (342) is received within a channel or track of outer housing (14) or an intermediate internal housing, such a channel or track may include an opening or additional channel to prevent lower portion (344) to extend through such a channel or track to receiving feature (32) of piercer (22).

Piercer retraction assembly (350) is disposed proximally of cocking member (310) and actuation member (330). As will be described in greater detail below, piercer retraction assembly (350) is generally configured to axially translate piercer drive assembly (300) relative to lead screw (112). Piercer retraction assembly (350) comprises a first retraction member (352) and a second retraction member (370), and a retainer (390) disposed between first retraction member (352) and second retraction member (370).

First retraction member (352) comprises a body (354) and a support arm (360). Body (354) defines a bore (356) extending entirely through body (354). Body (354) further includes a counter-bore (358) disposed adjacent to bore (356). Counter-bore (358) extends distally only partially though body (354) from the proximal end thereof. As will be described in greater detail below, bore (356) and counter-bore (358) are generally sized to receive slide portion (316) of cocking member (310) and slide portion (140) of carriage nut (130). Bore (356) defines a diameter that is generally undersized relative to a diameter defined by retainer (390), while counter-bore (358) defines a diameter that is generally oversized relative to the diameter defined by retainer (390). As will be described in greater detail below, this difference in diameter between bore (356) and counter-bore (358) is configured to secure retainer (390) between first retraction member (352) and second retraction member (370).

Support arm (360) of first retraction member (352) extends distally from body (354). The distal extension of support arm (360) defines a length that is generally equivalent to spring (302) in a compressed state. On the distal end of support arm (360), support arm (360) defines a receiving indentation (362). Receiving indentation (362) is generally configured to receive at least a portion of release member (338) of actuation member (330). As will be described in greater detail below, receiving indentation (362) is generally configured to operate in conjunction with at least a portion of release assembly (400) to selectively hold release member (338) in a predetermined position relative to first retraction member (352).

Second retraction member (370) comprises a body (372) having a generally rectangular shape. Body (372) defines a bore (374) and a counter-bore (376) disposed coaxially with bore (374). Bore (374) extends entirely though body (372), while counter-bore (376) extends distally through only a portion of body (372) from the distal end thereof. Bore (374) and counter-bore (376) are both configured to receive at least a portion of lead screw (112) such that lead screw (112) can extend entirely though second retraction member (370). However, a diameter defined by counter-bore (376) is larger than a diameter defined by bore (374) to accommodate retainer (390) within counter-bore (376). It should be understood that this differential in the diameters of bore (374) and counter-bore (376) is configured to prevent proximal movement of retainer (390) relative to second retraction member (370) such that retainer (390) is generally held between first retraction member (352) and second retraction member (370).

Bore (374) further includes a protrusion (378) extending downwardly into the space defined by bore (374). Protrusion (378) comprises a generally cylindrical shape, although any other suitable shape may be used. As will be described in greater detail below, protrusion (378) is configured to engage threads (125) of lead screw (112) to drive translation of second retraction member (370) in response to rotation of lead screw (112).

As described above, retainer (390) is disposed between first retraction member (352) and second retraction member (370). Retainer (390) generally comprises a circular shape similar to a washer or other similar structure. Retainer (390) includes a bore (392) extending entirely though retainer (390). Bore (392) of retainer (390) is sized to permit retainer (390) to fit within annular channel (142) of carriage nut (130). Because retainer (390) is secured between first retraction member (352) and second retraction member (370), it should be understood that when retainer (390) generally axially secures movement of carriage nut (130) relative to piercer retraction assembly (350) via engagement between retainer (390) and annular channel (142). Thus, it should be understood that axial movement of carriage nut (130) will generally result in axial movement of piercer retraction assembly (350). As will be described in greater detail below, this relationship between movement of carriage nut (130) and piercer retraction assembly (350) generally results in retraction of piercer (22) during the tissue acquisition cycle.

While retainer (390) axially secures movement of carriage nut (130) relative to piercer retraction assembly (350), it should be understood that carriage nut (130) is rotatably movable relative to piercer retraction assembly (350). In other words, retainer (390) only secures axial movement of carriage nut (130), not rotational movement. Although not shown, it should be understood that in some examples retainer (390) can be adjacent to one or more bearings to disposed within either or both counter-bores (358, 376) of first retraction member (352) and second retraction member (370), respectively. In such examples, bearings can be used to promote the rotatability of carriage nut (130) relative to piercer retraction assembly (350). Additionally, although retainer (390) is shown as having a generally circular shape, it should be understood that in some examples retainer (390) may comprise a variety of other shapes. For instance, in other examples retainer (390) comprises a c-washer, a snap-on washer, a circlip, a Jesus clip, and/or any other suitable retaining feature as will be apparent to those of ordinary skill in the art in view of the teachings herein.

When piercer drive assembly (300) is assembled (e.g., as seen in FIG. 4), spring (302) is disposed between the proximal end of actuation member (330) and the distal end of body (354) of first retraction member (352). In addition, spring (302) is disposed coaxially around slide portion (316) of cocking member (310) and/or coaxially around slide portion (140) of carriage nut (130), depending on the particular stage of operation of drive assembly (100). As will be described in greater detail below, spring (302) is generally configured to drive actuation member (330) distally after actuation member (330) is released by release assembly (400). Spring (302) generally defines an outer diameter that approximately corresponds to the outer diameter of slide portion (316) of cocking member (310). Although spring (302) of the present example is shown as a coil spring, it should be understood that any other suitable resilient member may be used as will be apparent to those of ordinary skill in the art in view of the teachings herein.

Figure 12:
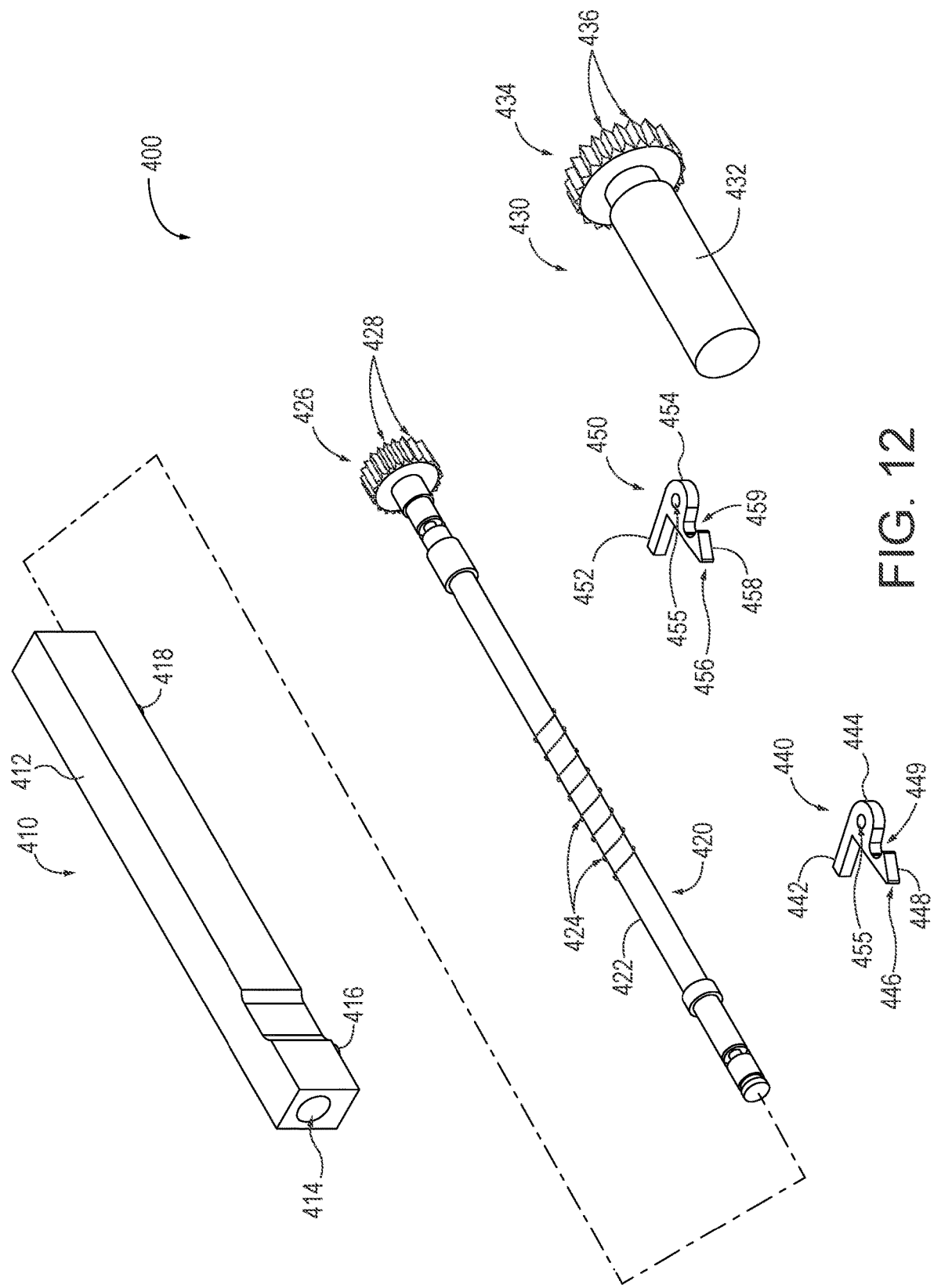
FIG. 12 depicts an exploded view of a release assembly of the drive assembly of FIG. 4.
Figure 13:
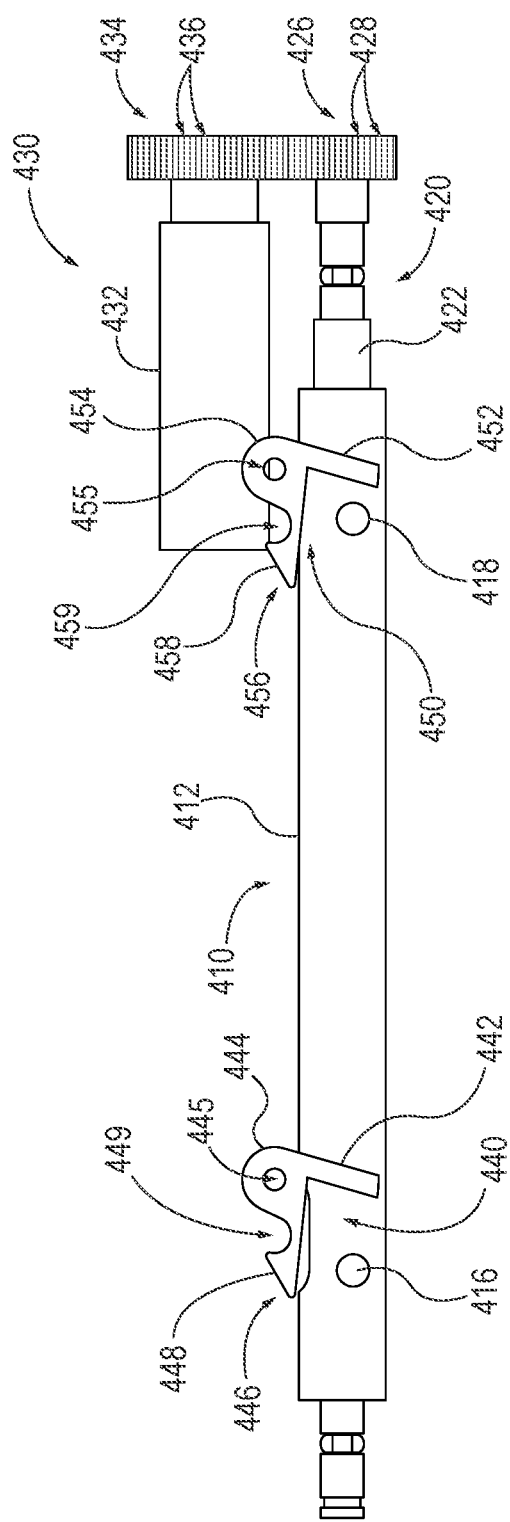
FIG. 13 depicts a bottom plan view of the release assembly of FIG. 4.

FIGS. 12 and 13 show release assembly (400) in greater detail. As can be seen, release assembly (400) comprises a nut member (410), a secondary lead screw (420), a motor assembly (430), a first latch member (440), and a second latch member (450). Nut member (410) comprises a body (412) with an elongate bore (414) extending longitudinally therethrough. Although not shown, it should be understood that within body (412), bore (414) includes a threaded portion (not shown) including threads (not shown) extending into bore (414). As will be described in greater detail below, threaded portion of bore (414) is configured to engage at least a portion of secondary lead screw (420) to permit secondary lead screw (420) to drive proximal and distal translation of nut member (410).

Nut member (410) further includes a first latch actuator (416) and a second latch actuator (418) extending downwardly from body (412). Both first latch actuator (416) and second latch actuator (418) comprise a generally cylindrical shape, although any other suitable shape may be used. First latch actuator (416) is associated with first latch member (440), while second latch actuator (418) is associated with second latch member (450). As will be described in greater detail below, latch actuators (416, 418) are generally configured to engage with a corresponding latch member (440, 450) to release cutter drive assembly (200) and piercer drive assembly (300) to fire cutter (40) and piercer (22), respectively.

Secondary lead screw (420) comprises a drive rod (422) and a drive member (426). Drive rod (422) defines a generally cylindrical shape with a plurality of threads (424) extending along at least a portion of the length of drive rod (422). Threads (424) are configured to engage corresponding threads disposed within nut member (410). This engagement between threads (424) of drive rod (422) and the threads of nut member (410) generally results in the conversion of rotation motion of secondary lead screw (420) into translation of nut member (410). As will be described in greater detail below, this motion of nut member (410) via lead screw (420) is generally configured to selectively initiate firing of cutter (40) and piercer (22).

Drive member (426) of secondary lead screw (420) is fixedly secured to the proximal end of drive rod (422). Drive member (426) is configured to impart rotary motion onto drive rod (422) from motor assembly (430). In particular, drive member (426) comprises a plurality of teeth (428). As will be described in greater detail below, teeth (428) are configured to engage at least a portion of motor assembly (430) such that rotatory motion provided by motor assembly (430) is communicated to drive rod (422) via teeth (428) of drive member (426).

Motor assembly (430) assembly comprises a rotary power source (432) and a drive member (434) in rotary communication with rotary power source (432). Rotary power source (432) in the present example is configured as an electrical motor. In other examples, rotary power source (432) can be configured as a variety of other rotary power sources such as pneumatic motors, piezoelectric motors, and/or etc.

Drive member (434) of motor assembly (430) is configured to communicate rotary power from rotary power source (432) to secondary lead screw (420). In particular, drive member (434) comprises a plurality of teeth (436) that are configured to engage with teeth (428) of drive member (426) described above with respect to secondary lead screw (420). Though engagement between teeth (428, 436), drive members (426, 434) are rotated, thereby communicating rotary power from motor (432) to drive member (426) of secondary lead screw (420). Although drive members (426, 434) are described herein as being essentially gears with teeth (428, 436), it should be understood that in other examples any other suitable rotary transmission may be used. By way of example only, suitable rotary transmissions may include a belt drive, a drive with additional gears to provide a gear ratio between motor (432) and drive rod (422), and/or etc.

First latch member (440) comprises lever portion (442), a pivot portion (444), and a catch portion (446). Lever portion (442), pivot portion (444), and catch portion (446) are all integrally connected to form L-shaped structure. Lever portion (442) and catch portion (446) each define one leg of the L-shape, pivot portion (444) is disposed between lever portion (442) and catch portion (448). Pivot portion (444) includes an opening (445) extending entirely through latch member (440) such that a pin or other similar structure may be received by opening (445) for pivoting of first latch member (440) about an axis defined by opening (445). As will be described in greater detail below, this pivoting action generally permits first latch member (440) to selectively catch and release release member (238) of cutter drive assembly (200).

Catch portion (446) defines a ramp feature (448) and a recessed feature (449). Ramp feature (448) is generally triangular in shape, while adjacent recessed feature (449) is generally semicircular. Both ramp feature (448) and recessed feature (449) are configured to engage release member (238) of cutter drive assembly (200). For instance, and as will be described in greater detail below, ramp feature (448) functions to pivot first latch member (440) away from release member (238) to a receiving or releasing position so that release member (238) can enter recessed feature (449). Similarly, recessed feature (449) catches or otherwise selectively secures release member (238) when first latch member (440) is pivoted to a cocked position. Although not shown herein, it should be understood that in some examples, first latch member (440) may include a resilient feature to resiliently bias first latch member (440) toward the cocked position once release member (238) is received by recessed feature (449).

Second latch member (450) comprises lever portion (452), a pivot portion (454), and a catch portion (456). Lever portion (452), pivot portion (454), and catch portion (456) are all integrally connected to form an L-shaped structure. Lever portion (452) and catch portion (456) each define one leg of the L-shape, pivot portion (454) is disposed between lever portion (452) and catch portion (458). Pivot portion (454) includes an opening (455) extending entirely through latch member (450) such that a pin or other similar structure may be received by opening (455) for pivoting of second latch member (450) about an axis defined by opening (455). As will be described in greater detail below, this pivoting action generally permits second latch member (450) to selectively catch and release release member (338) of piercer drive assembly (300).

Catch portion (456) defines a ramp feature (458) and a recessed feature (459). Ramp feature (458) is generally triangular in shape, while adjacent recessed feature (459) is generally semicircular. Both ramp feature (458) and recessed feature (459) are configured to engage release member (338) of piercer drive assembly (300). For instance, and as will be described in greater detail below, ramp feature (458) functions to pivot second latch member (450) away from release member (338) to a receiving or releasing position so that release member (338) can enter recessed feature (459). Similarly, recessed feature (459) catches or otherwise selectively secures release member (338) when second latch member (450) is pivoted to a cocked position. Although not shown herein, it should be understood that in some examples, first latch member (450) may include a resilient feature to resiliently bias first latch member (450) toward the cocked position once release member (338) is received by recessed feature (459).

FIGS. 14-26 show an exemplary use of biopsy device (10) described above. In particular, in such a use, drive assembly (100) is generally used to cock and then fire piercer (22) and cutter (40) in a predetermined sequence to penetrate a suspicious lesion and then sever a tissue sample thereof. Once piercer (22) and cutter (40) are fired, piercer (22) is retracted relative to cutter (40) to permit collection of the severed tissue by an operator. The cocking and firing process may then be repeated as many times as desired to collect as many tissue samples as desired by the user.

Figure 14:
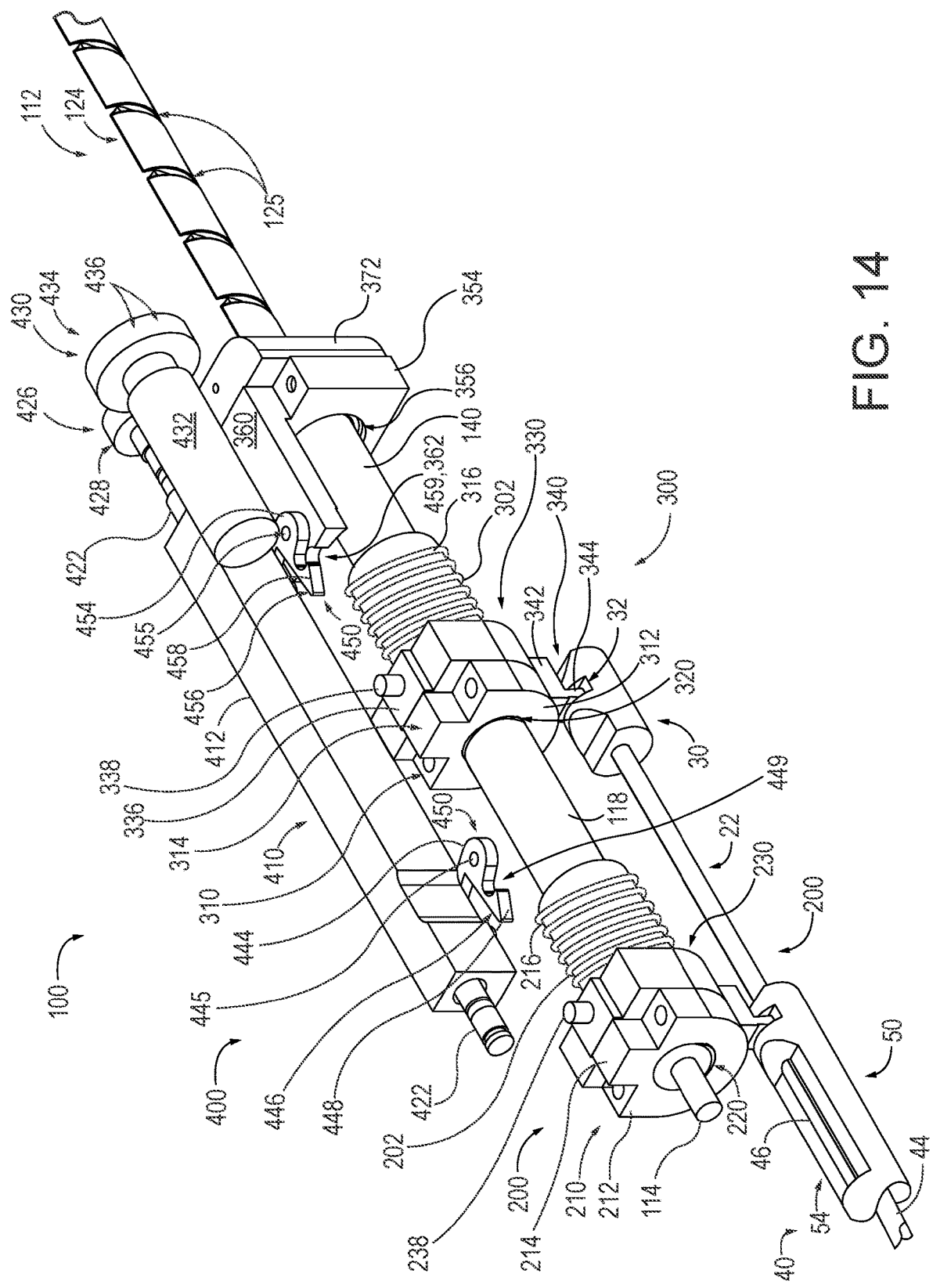
FIG. 14 depicts another perspective view of the drive assembly of FIG. 4, with the drive assembly in an initial position.
Figure 15:
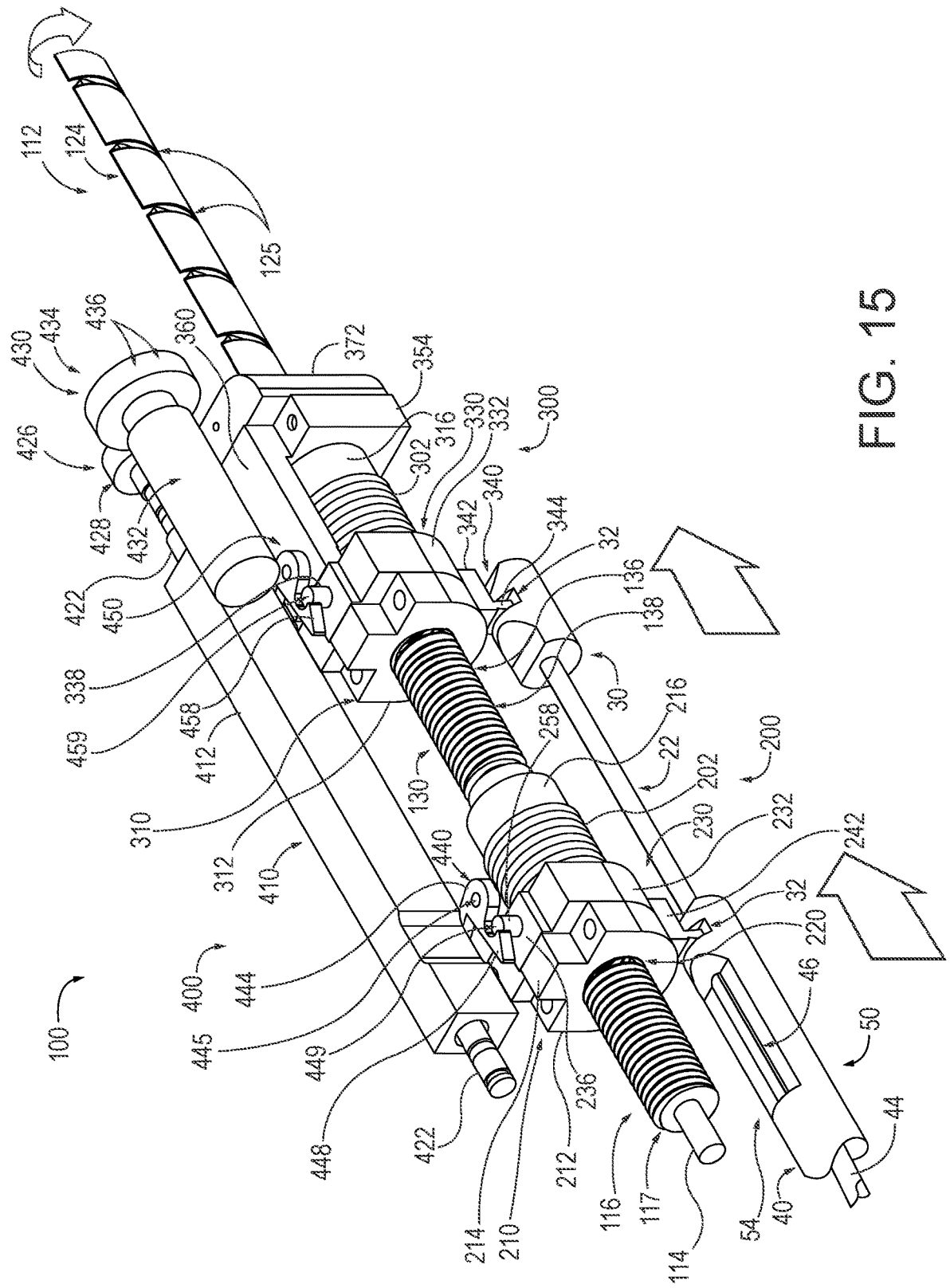
FIG. 15 depicts still another perspective view of the drive assembly of FIG. 4, with the drive assembly in a cocked position.
Figure 16:
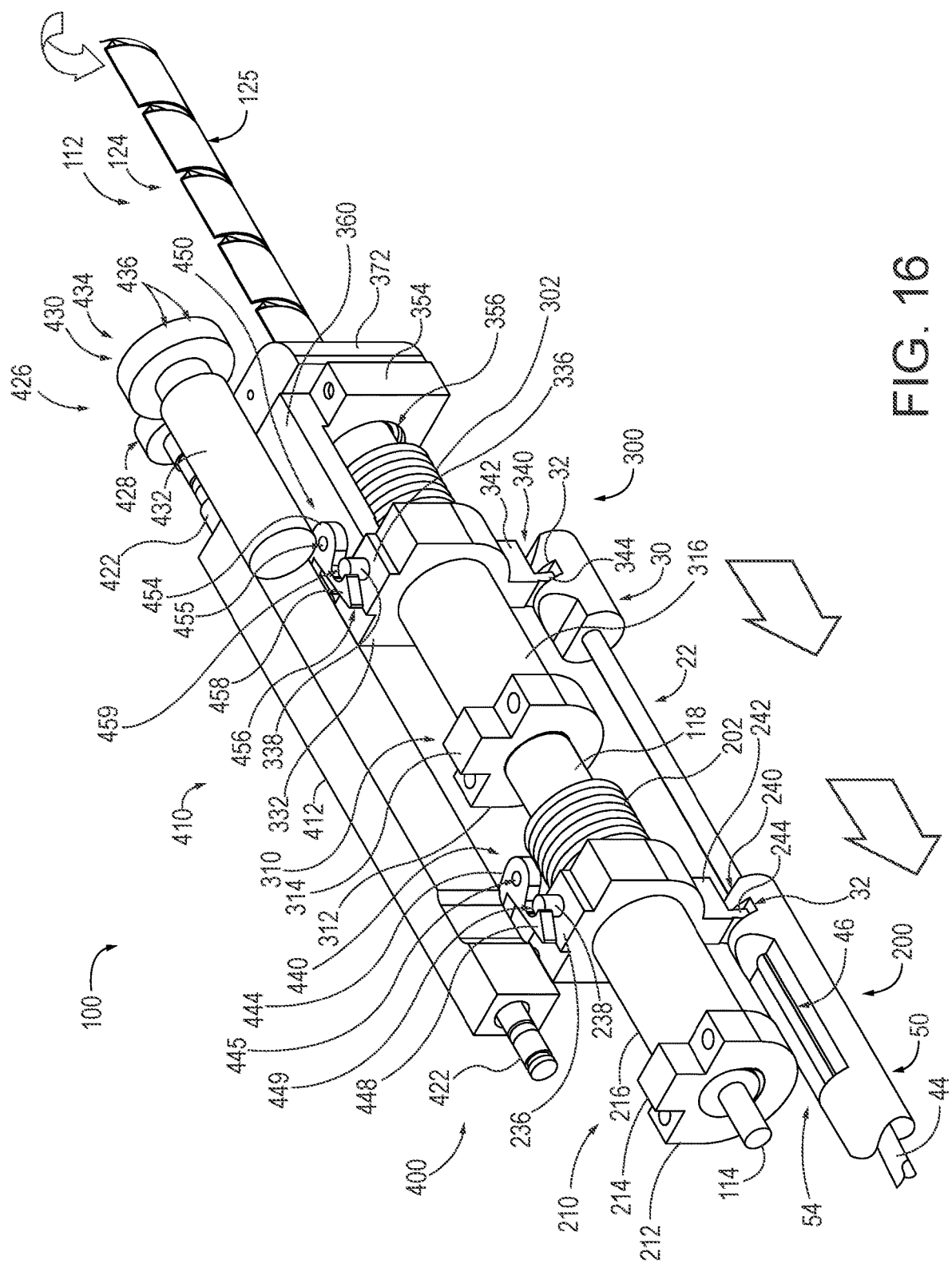
FIG. 16 depicts yet another perspective view of the drive assembly of FIG. 4, with the drive assembly in a ready position.

FIGS. 14-16 show an exemplary cocking sequence that results in piercer (22) and cutter (40) being prepared for firing. In the cocking sequence, drive assembly (100) can begin in an initial position as shown in FIG. 15. Alternatively, and as will be described in greater detail below, drive assembly (100) may begin in a cocked position as shown in FIG. 15. In the initial position, piercer (22) and cutter (40) are each in a distal position. Correspondingly, cutter drive assembly (200) and piercer drive assembly (300) are also in a distal uncocked position. Release assembly (400) is disengaged from both cutter drive assembly (200) and piercer drive assembly (300) when cutter drive assembly (200) and piercer drive assembly (300) are in the distal position.

When cutter drive assembly (200) is in the distal position, cocking member (210) is positioned on the distal end of first threaded portion (116) of lead screw (112). Actuation member (230) is positioned adjacent to stop portion (212) of cocking member (210) via spring (202). In particular, because release member (238) of actuation member (230) is disengaged from release assembly (400), release member (238) is freely movable along the axis of lead screw (112). Despite actuation member (230) being freely movable along the axis of lead screw (112), spring (202) is resiliently biased to urge actuation member (230) distally into the position shown in FIG. 14. Thus, actuation member (230) is urged adjacent to cocking member (210) by spring (202).

When piercer drive assembly (300) is in the distal position, cocking member (310) is positioned on the distal end of threaded portion (136) of carriage nut (130). Carriage nut (130) is correspondingly positioned on the distal end of second threaded portion (124) of lead screw (112) such that cocking member (310) is in the distal most position relative to both carriage nut (130) and lead screw (112). Actuation member (330) is positioned adjacent to stop portion (312) of cocking member (310) via spring (302). In particular, because release member (338) of actuation member (330) is disengaged from release assembly (400), release member (338) is freely movable along the axis of lead screw (112) and carriage nut (130). Despite actuation member (330) being freely movable along the axis of lead screw (112) and carriage nut (130), spring (302) is resiliently biased to urge actuation member (330) distally into the position shown in FIG. 14. Thus, actuation member (330) is urged adjacent to cocking member (310) by spring (302).

In the initial position, piercer retraction assembly (350) of piercer drive assembly (300) is also in a distal position. However, when piercer retraction assembly (350) is in the distal position, piercer retraction assembly (350) is generally separate from cocking member (310) and actuation member (330). As described above, piercer retraction assembly (350) is axially fixed relative to carriage nut (130) by engagement between retainer of retraction assembly (350) and annular channel (142) of carriage nut (130). Because of this, piercer retraction assembly (350) is axially fixed near the distal end of carriage nut (130) with axial movement of piercer retraction assembly (350) only resulting from axial movement of carriage nut (130).

To move drive assembly (100) into the cocked position, an operator may actuate actuation member (16) on the exterior of outer housing (14). Actuation of actuation member (16) then provides a signal to rotary power source (164) of needle cocking assembly (110). Upon receiving such a signal, rotary power source (164) begins rotating lead screw (112) via rotary communication features (152, 162) in a first direction as shown in FIG. 15.

Rotation of lead screw (112) in the first direction generally causes cutter drive assembly (200) and piercer drive assembly (300) to translate proximally. In particular, rotation of lead screw (112) causes threads (117) of first threaded portion (118) to engage threads (222) of cocking member (210). This engagement between threads (117, 222) causes cocking member (210) to translate proximally. As cocking member (210) is translated proximally, stop portion (212) of cocking member (210) engages actuation member (230) to correspondingly push actuation member (230) proximally. Actuation member (230) in turn acts on spring (202) to thereby compress spring (202).

Proximal translation of cocking member (210) and actuation member (230) continues until release member (238) contacts first latch member (440) of release assembly (410). Once such contact is made, release member (238) of actuation member (230) engages ramp feature (448) of first latch member (440) to pivot first latch member (440) outwardly (e.g., into the page of FIG. 15) as actuation member (230) is driven proximally. Proximal translation of actuation member (230) and pivoting of first latch member (440) will continue until release member (238) is adjacent to recessed feature (449) of first latch member (440).

Once release member (238) of actuation member (230) is adjacent to recessed feature (449) of first latch member (440), rotation of lead screw (112) and corresponding proximal translation of actuation member (230) via cocking member (210) will stop. At this stage, first latch member (440) will have pivoted inwardly (e.g., out of the page of FIG. 15) to capture release member (238) of actuation member (230) within recessed feature (449) of first latch member (440). Once release member (238) is captured within recessed feature (449), actuation member (230) will be generally held in the axial position shown in FIG. 15 via first latch member (440).

Rotation of lead screw (112) also rotates carriage nut (130) via key (134) of carriage nut (130) and keyway (122) of lead screw (112). Upon rotation of carriage nut (130) piercer drive assembly (300) is generally translated proximally. In particular, upon rotation of carriage nut (130), threads (138) of carriage nut (130) engage threads (322) disposed within bore (320) of cocking member (310). The engagement between threads (138, 322) causes cocking member (310) to translate proximally. As cocking member (310) is translated proximally, stop portion (312) of cocking member (310) engages actuation member (330) to correspondingly push actuation member (330) proximally. Actuation member (330) in turn acts on spring (302) to thereby compress spring (302).

Proximal translation of cocking member (310) and actuation member (330) continues until release member (338) contacts second latch member (450) of release assembly (410). Once such contact is made, release member (338) of actuation member (330) engages ramp feature (458) of second latch member (450) to pivot second latch member (450) outwardly (e.g., into the page of FIG. 15) as actuation member (330) is driven proximally. Proximal translation of actuation member (330) and pivoting of second latch member (450) will continue until release member (338) is adjacent to recessed feature (459) of second latch member (450).

Once release member (338) of actuation member (330) is adjacent to recessed feature (459) of second latch member (450), rotation of carriage nut (130) via lead screw (112) and corresponding proximal translation of actuation member (330) via cocking member (310) will stop. At this stage, second latch member (450) will have pivoted inwardly (e.g., out of the page of FIG. 15) to capture release member (338) of actuation member (330) within recessed feature (459) of second latch member (450). Once release member (338) is captured within recessed feature (459), actuation member (330) will be generally held in the axial position shown in FIG. 15 via second latch member (450).

Once both cutter drive assembly (200) and piercer drive assembly (300) are translated to the proximal positions shown in FIG. 15, drive assembly (100) is in a cocked position. Although drive assembly (100) is shown and described herein as initially transitioning to the cocked position from the initial position, it should be understood that in some examples the procedure may begin with drive assembly (100) being in the cocked position. Regardless, in the cocked position, springs (202, 302) are compressed for firing. However, because each cocking member (210, 310) is adjacent to each actuation member (230, 330), cutter (40) and piercer (22) cannot be fired. Thus, it should be understood that when drive assembly (100) is in the cocked position, cutter (40) and piercer (22) are merely in position for firing, but drive assembly (100) is not yet fully armed.

While drive assembly (100) is in the cocked position, an operator may inert needle assembly (20) into tissue of a patient. As shown in FIG. 19, insertion may be performed to position needle assembly (20) adjacent to a suspicious lesion (LE). In some uses, inserting needle assembly (20) into tissue of a patient may be desirable to prevent inadvertent firing of piercer (22) or cutter (40). Of course, it should be understood that an operator may position needle assembly (20) when drive assembly (100) is in other positions, as will be described in greater detail below.

To prepare needle assembly (20) for firing, an operator may transition drive assembly (100) from the cocked position shown in FIG. 15 to a ready position shown in FIG. 16. To initiate the transition of drive assembly (100) from the cocked position to the ready position, an operator may push actuation member (16) a second time. Pressing actuation member (16) once again sends a signal to rotary power source (164) of needle cocking assembly (110) to initiate rotation of lead screw (112) in a second direction, opposite of the first direction.

Rotation of lead screw (112) in the opposite direction generally causes cocking member (210) of cutter drive assembly (200) and cocking member (310) of piercer drive assembly (300) to each translate distally relative to lead screw (112). In particular, threads (117) of first threaded portion (116) again engage threads (222) of cocking member (210). However, due to rotation of lead screw (112) in the second direction, this engagement causes cocking member (210) to translate distally. Because actuation member (230) and spring (202) are not fixedly secured to cocking member (210), actuation member (230) and spring (202) remain held in position by first latch member (440) of release assembly (400). Translation of cocking member (210) continues until cocking member (210) reaches the distal end of first threaded portion (116) of lead screw (112) as shown in FIG. 16.

Similarly, with respect to piercer drive assembly (300), threads (138) of carriage nut (130) again engage threads (322) of cocking member (310). As described above, rotation of lead screw (112) results in rotation of carriage nut (130) via engagement between key (134) and keyway (122). Accordingly, rotation of lead screw (112) causes carriage nut (130) to rotate in the second direction. Rotation of carriage nut (130) in the second direction causes cocking member (310) to translate distally via engagement of threads (138, 322). Because actuation member (330) and spring (302) are not fixedly secured to cocking member (310), actuation member (330) and spring (302) remain held in position by second latch member (450) of release assembly (400). Translation of cocking member (310) continues until cocking member (310) reaches the distal end of threaded portion (136) of carriage nut (130) as shown in FIG. 16.

Once cocking member (210) of cutter drive assembly (200) and cocking member (310) of piercer drive assembly (300) are positioned in the distal position as shown in FIG. 16, drive assembly (100) is in the ready position. Once drive assembly (100) is in the ready position, an operator may position needle assembly (20) into tissue of a patient adjacent to suspicious lesion (LE) as shown in FIG. 19, if operator had not already done so prior to transitioning drive assembly (100) from the cocking position to the ready position.

With drive assembly (100) in the ready position (FIG. 16), and needle assembly (20) placed near a suspicious lesion (SE) (FIG. 19), an operator may next initiate a firing sequence. FIGS. 17-18, and 19-21 show the firing sequence in greater detail. To initiate the firing sequence, an operator may press actuation member (16) on outer housing (14) a third time. When actuation member (16) is pressed, a signal now sent to motor (432) of release assembly (400). This signal causes motor (432) to supply rotary power to secondary lead screw (420) via drive members (426, 434) to thereby rotate secondary lead screw (420). As secondary lead screw (420) rotates, threads (424) of secondary lead screw (420) engage the threads disposed within body (412) of nut member (410).

Engagement between threads (424) of secondary lead screw (420) and the threads of nut member (410) during rotation of secondary lead screw (420) causes nut member (410) to retract proximally. As nut member (410) retracts proximally, second latch actuator (418) first comes into contact with lever portion (452) of second latch member (450). Due to the spacing between first latch actuator (416) and second latch actuator (418), it should be understood that only second latch actuator (418) contacts second latch member (450) initially. As will be described in greater detail below, further proximal actuation of nut member (410) is needed for first latch actuator (416) to engage lever portion (442) of first latch member (440).

Figure 17:
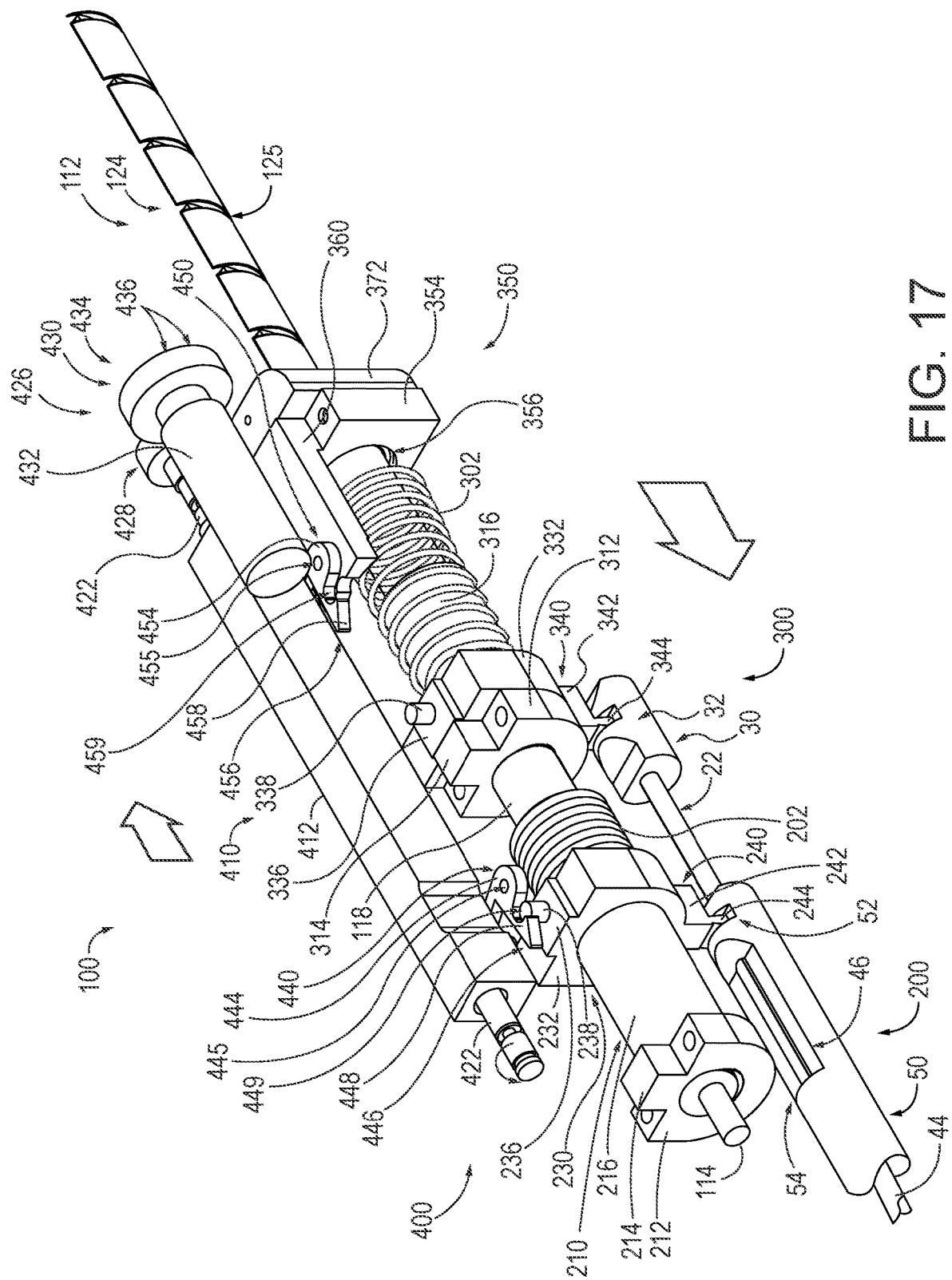
FIG. 17 depicts yet another perspective view of the drive assembly of FIG. 4, with the piercer drive assembly in a fired position.

As nut member (410) continues to translate proximally, second latch actuator (418) engages lever portion (452) of second latch member (450) to begin to pivot second latch member (450) away from release member (338) of piercer drive assembly (300). Further proximal translation of nut member (410) eventually results in second latch member (450) fully pivoting to disengage release member (338) from recessed feature (459) of second latch member (450) as shown in FIG. 17.

Once release member (338) is disengaged from recessed feature (459) of second latch member (450), actuation member (330) is free to translate axially relative to lead screw (112). Because spring (302) was previously compressed during cocking, spring (302) will now rapidly urge actuation member (330) distally. As described above, actuation member (330) includes actuation tab (340), which is secured to receiving feature (32) of piercer (22). Thus, it should be understood that rapid translation of actuation member (330) will result in corresponding rapid translation of piercer (22). Rapid translation of piercer (22) will result in distal tip (24) and notch (26) of piercer (22) penetrating through suspicious lesion (LE) as shown in FIG. 20.

Once firing of piercer (22) has occurred, motor (432) of release assembly (400) will stop, thereby stopping further proximal movement of nut member (410) via secondary lead screw (420). In the present use, proximal translation of nut member (410) will stop prior to first latch actuator (416) reaching first latch member (440) for firing of cutter (40). In other words, after piercer (22) is fired, the firing sequence is paused prior to firing cutter (40). Alternatively, in some uses, motor (432) may continue rotating without stopping after firing of piercer (22). In these uses, piercer (22) is fired first, followed by a relatively short delay, and then cutter (40) is fired using the sequence described below.

Figure 18:
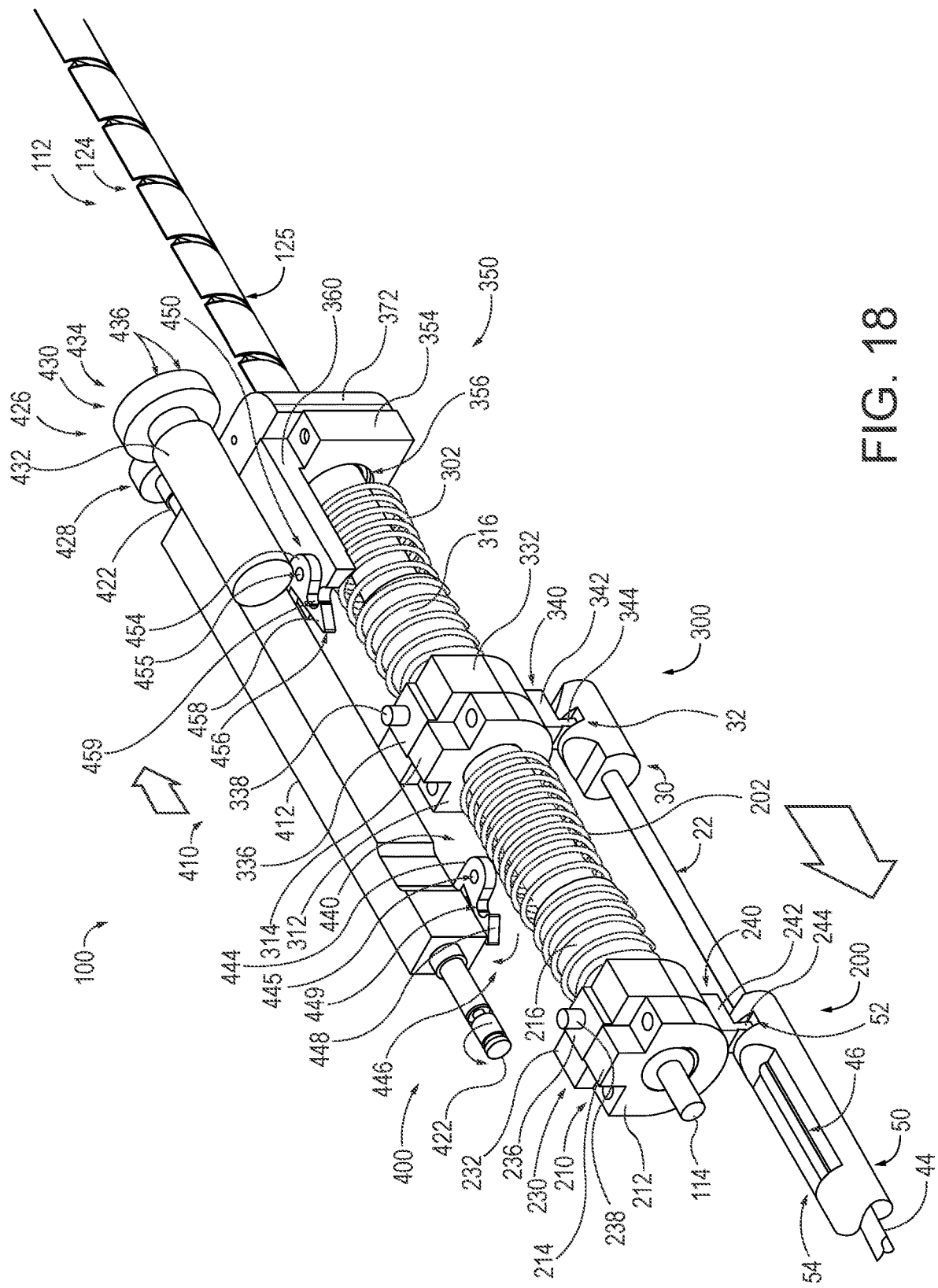
FIG. 18 depicts yet another perspective view of the drive assembly of FIG. 4, with the cutter drive assembly in a fired position.

To fire cutter (40) under the present use, an operator may reinitiate rotation of motor (432) and corresponding proximal translation of nut member (410) by pressing actuation member (16) on outer housing (14) a fourth time. This causes motor (432) of release assembly (400) to continue rotation of secondary lead screw (420). As similarly described above, engagement between threads (424) of secondary lead screw (420) and the threads of nut member (410) during rotation of secondary lead screw (420) causes nut member (410) to retract proximally. As nut member (410) continues to retract proximally first latch actuator (416) will engage lever portion (442) of first latch member (440). Further proximal translation of nut member (410) will result in first latch actuator (416) pushing lever portion (442) to pivot first latch member (440) away from release member (238) of actuation member (230) as shown in FIG. 18. This pivoting of first latch member (440) will eventually result in disengagement of release member (238) of actuation member (230) from first latch member (440).

Figure 21:
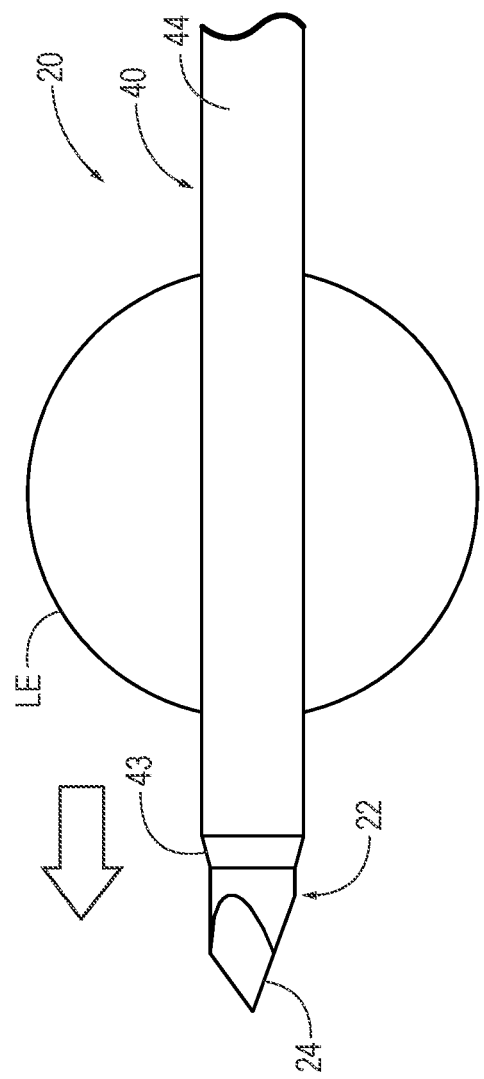
FIG. 21 depicts still another partial front elevational view of the needle assembly of FIG. 2, with a cutter fired through the lesion.

With release member (238) of actuation member (230) disengaged from first latch member (440), actuation member (230) is free to translate axially relative to lead screw (112). Because spring (202) was previously compressed during cocking, spring (202) will now rapidly urge actuation member (230) distally. As described above, actuation member (230) includes actuation tab (240), which is secured to receiving feature (52) of cutter (40). Thus, it should be understood that rapid translation of actuation member (230) will result in corresponding rapid translation of cutter (40). Rapid translation of cutter (40) will result in distal end (42) of cutter (40) penetrating through suspicious lesion (LE) as shown in FIG. 21 to sever a tissue sample into notch (26) of piercer (22).

FIGS. 22-25 show an exemplary sequence for retracting piercer (22) relative to cutter (40) to collect a tissue sample after the tissue sample has been acquired using the firing sequence described above. As will be described in greater detail below, the piercer (22) retraction sequence generally involves retracting piercer (22) relative to cutter (40) to expose notch (26) of piercer within the tissue collection feature (54) of cutter (40). When piercer (22) is retracted in this way, an operator may extract a tissue sample from notch (26) for further analysis and processing.

Figure 24:
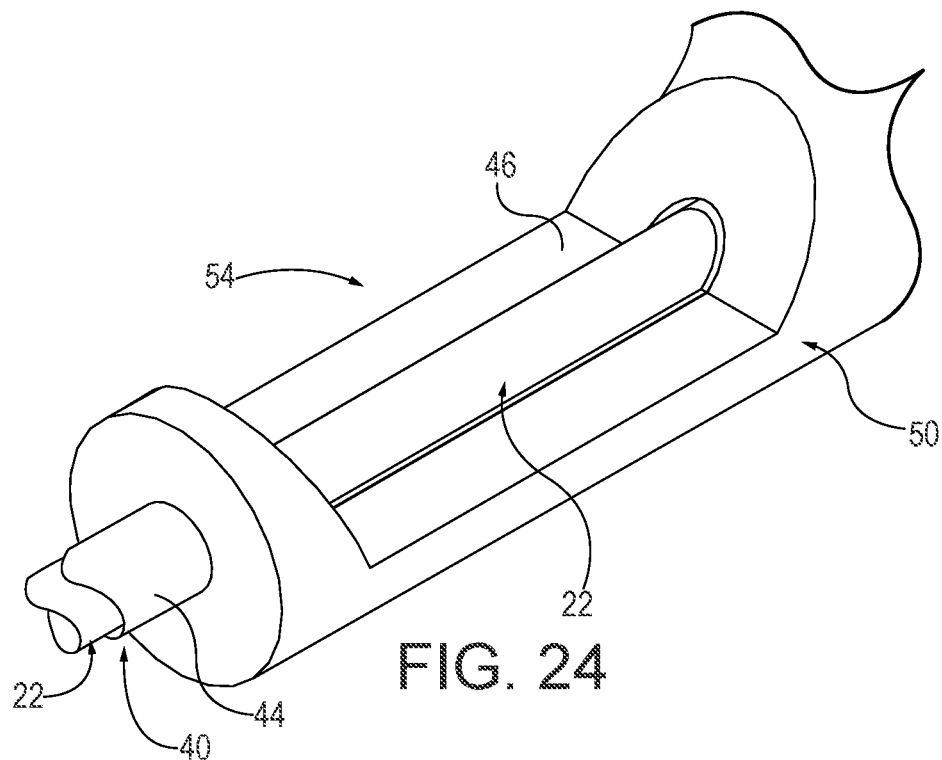
FIG. 24 depicts a detailed perspective view of a tissue collection feature of the needle assembly of FIG. 2, the tissue collection feature in a closed position.

The piercer (22) retraction sequence begins by returning drive assembly (100) to the cocked position described above with respect to FIG. 15. When drive assembly (100) is in the cocked position shown in FIGS. 4 and 15, piercer (22) is correspondingly disposed in a distal position. As can be seen in FIG. 24, when piercer is in the distal position, tissue collection feature (54) of cutter (40) is generally blocked by piercer (22). To return drive assembly (100) to the cocked position, an operator may press actuation member (16) on outer housing (14) a fifth time. As described above, drive assembly (100) is generally transitioned to the cocked position by rotating lead screw (112) in the first direction to translate cocking members (210, 310) of cutter drive assembly (200) and piercer drive assembly (300) proximally relative to lead screw (112).

Once drive assembly (100) is returned to the cocked position as shown in FIGS. 4 and 15, lead screw (112) continues to rotate in the first direction. As rotation continues, cocking members (210, 310) of cutter drive assembly (200) and piercer drive assembly (300) will begin to free-wheel relative to lead screw (112). In particular, cocking member (210) of cutter drive assembly (200) will disengage from first threaded portion (116) of lead screw (112) as cocking member (210) transitions to being adjacent to indented portion (119) of lead screw (112). Similarly, cocking member (310) of cutter drive assembly (300) will disengage from threaded portion (136) of carriage nut (130) as cocking member (310) transitions to being adjacent to indented portion (144) of carriage nut (130).

Figure 22:
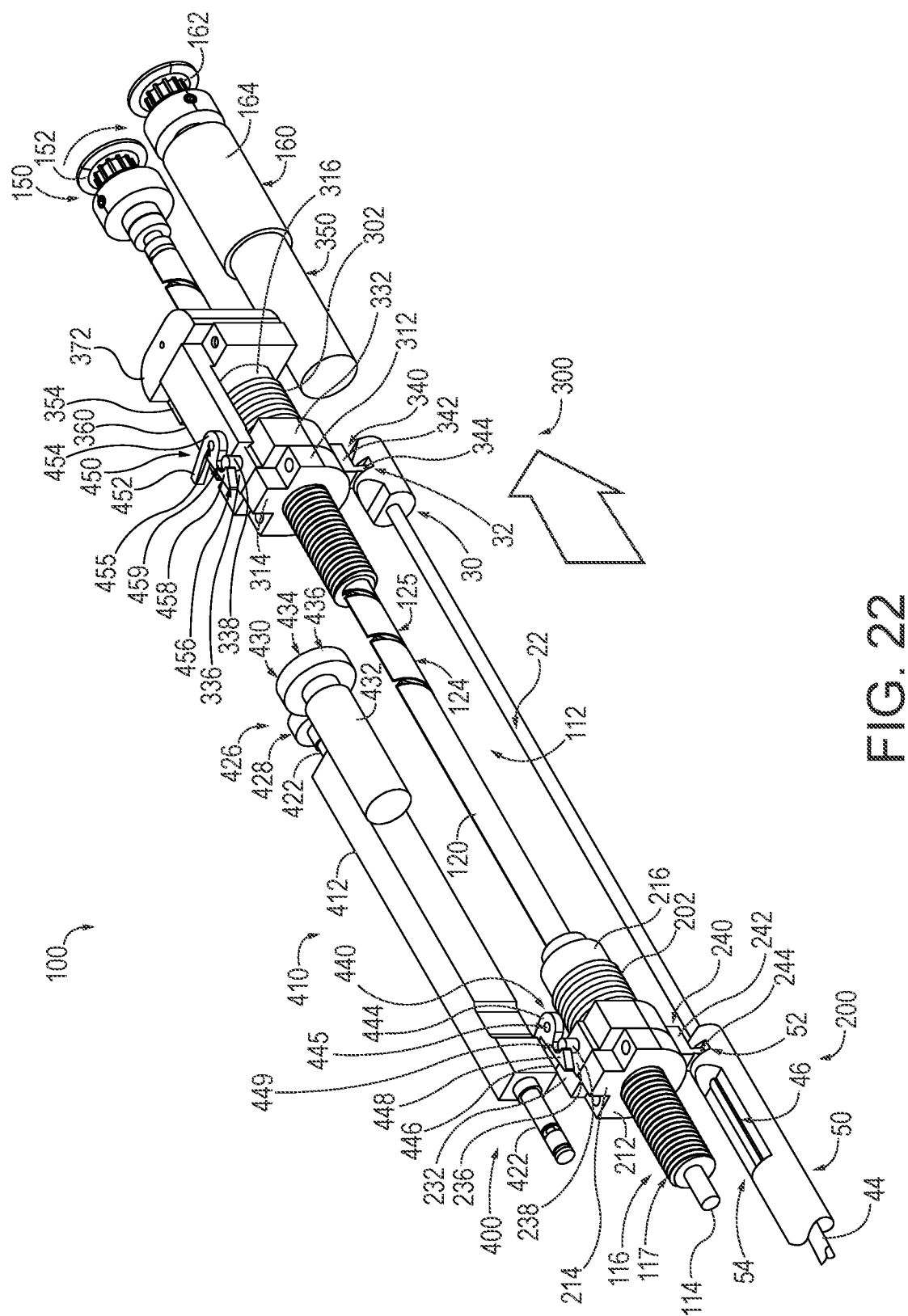
FIG. 22 depicts yet another perspective view of the drive assembly of FIG. 4, with a piercer retraction assembly retracted to an intermediate position.

As cocking members (210, 310) begin to free-wheel as described above, piercer retraction assembly (350) will begin to engage second threaded portion (124) of lead screw (112). In particular, protrusion (378) of second retraction member (370) is received by threads (125) of second threaded portion (124). As lead screw (112) rotates, engagement between protrusion (378) and threads (125) pulls second retraction member (370) proximally as shown in FIG. 22. Because second retraction member (370) is secured to first retraction member (352), proximal movement of second retraction member (370) also pulls first retraction member (352) proximally. Additionally, because retainer (390) is positioned between first retraction member (352) and second retraction member (370) to axially secure carriage nut (130) to piercer retraction assembly (350), proximal movement of first retraction member (352) and second retraction member (370) will result in corresponding proximal movement of carriage nut (130). With piercer drive assembly (300) disposed on carriage nut (130), translation of carriage nut (130) also results in translation of piercer drive assembly (300). Thus, it should be understood that as piercer retraction assembly (350) is driven proximally by rotation of lead screw (112), corresponding translation of piercer drive assembly (300) along with piercer (22) will result.

Figure 23:
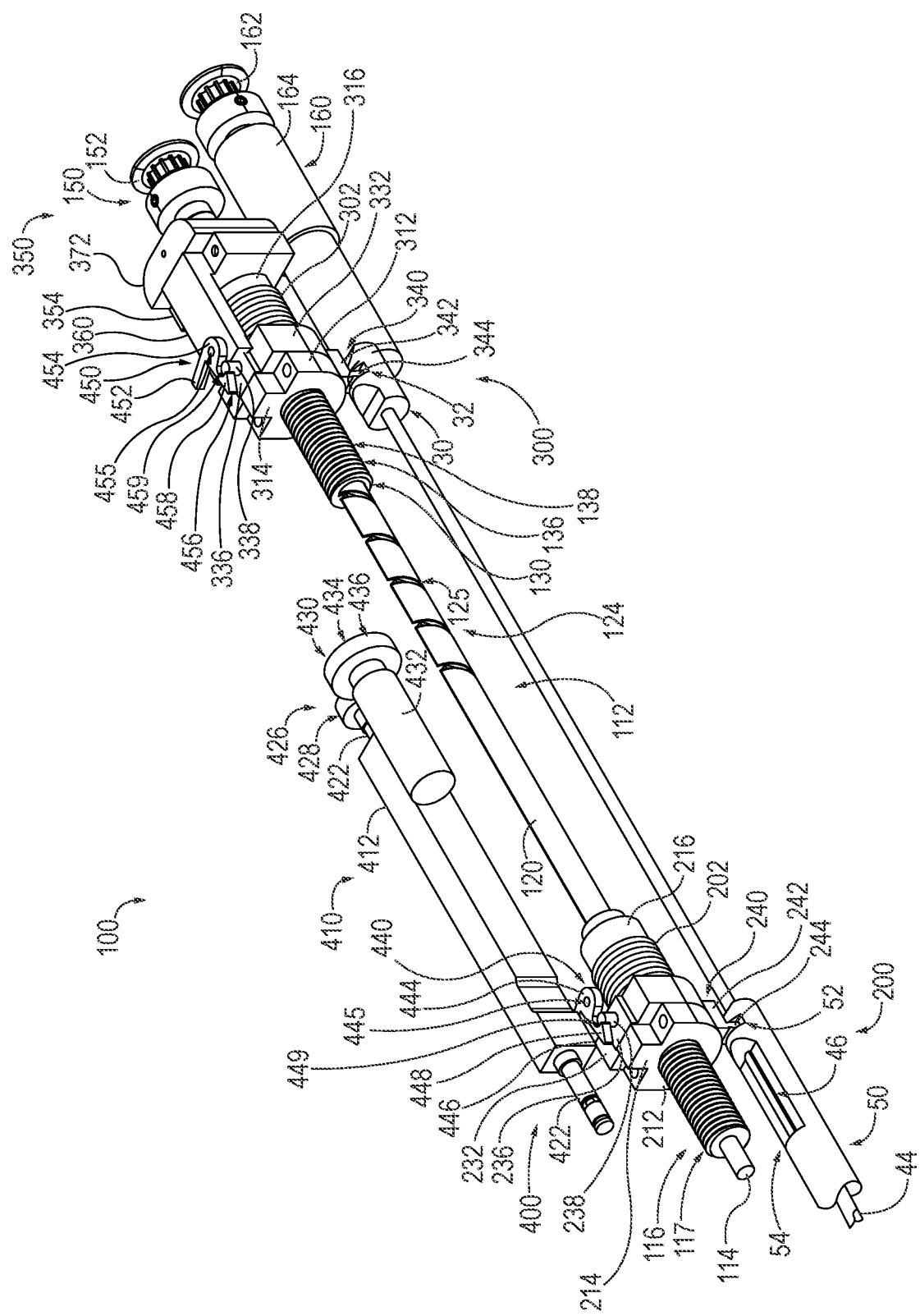
FIG. 23 depicts yet another perspective view of the drive assembly of FIG. 4, with the piercer retraction assembly of FIG. 22 retracted to a proximal position.

Proximal translation of piercer retraction assembly (350), piercer drive assembly (300), and piercer (22) continues until piercer retraction assembly (350) reaches the distal position shown in FIG. 23. Once piercer retraction assembly (350) reaches the distal position, rotation of lead screw (112) stops, thereby stopping further proximal translation of piercer retraction assembly (350).

Figure 25:
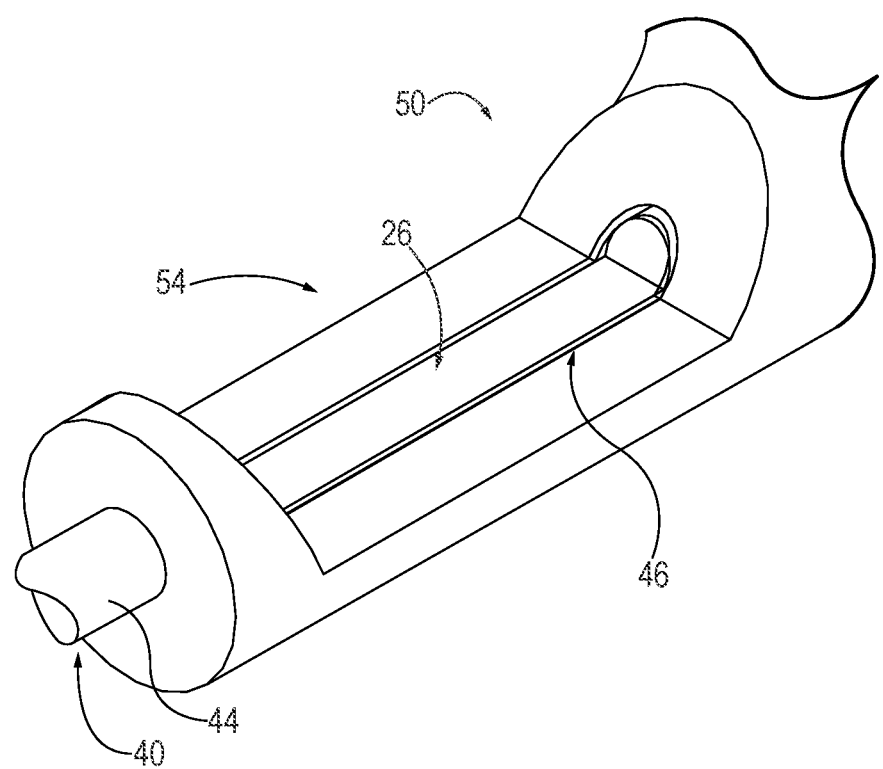
FIG. 25 depicts another detailed perspective view of the tissue collection feature of the needle assembly of FIG. 2, the tissue collection feature in an open position.

When piercer drive assembly (300) is in the distal position, piercer (22) is also in a distal position as shown in FIG. 25. As can be seen in FIG. 25, when piercer (22) is in the distal position, notch (26) of piercer (22) is aligned with tissue collection feature (54) of cutter (40). This alignment provides access to notch (26) through cut out (46) in cutter (40). At this stage, an operator may collect a tissue sample from notch (26) for further examination, analysis, investigation, and/or etc.

After having acquired a tissue sample, an operator may complete the biopsy procedure by removing biopsy device (10) from the patient. Alternatively, in some instances an operator may desire to collect additional samples using a single insertion of needle assembly (20) into a patient. In such instances, an operator may press actuation member (16) on outer housing (14) a sixth time. This will cause rotation communication feature (162) of needle cocking assembly to reactivate and return drive assembly (100) to the initial position or the cocking position via rotation of lead screw (112). An operator may then follow the same procedure described above one or more times until a desired number of tissue samples are collected.

Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A core needle biopsy device, comprising: a needle assembly, wherein the needle assembly includes a piercer and a hollow cutter, wherein the piercer includes a sharp distal tip and a notch proximal to the distal tip, wherein the piercer is slidably disposed within the cutter to sever a tissue sample into the notch of the piercer; a cutter drive assembly, wherein the cutter drive assembly is configured to selectively fire the cutter; a piercer drive assembly, wherein the piercer drive assembly is configured to selectively fire the piercer; and a piercer retraction assembly, wherein the piercer retraction assembly is configured to retract the piercer independently of the cutter while the needle assembly is disposed within a patient to expose the notch of the piercer to an exterior of a patient while at least a portion of the piercer remains within the cutter.

Example 2

The core needle biopsy device of Example 1, further comprising a needle cocking assembly, wherein the needle cocking assembly is configured to move at least a portion of the cutter drive assembly, the piercer drive assembly, and the piercer retraction assembly.

Example 3

The core needle biopsy device of Example 2, wherein the needle cocking assembly includes a lead screw, wherein the lead screw includes a first threaded portion and a second threaded portion, wherein the first threaded portion includes threads having a first pitch, wherein the second threaded portion includes threads having a second pitch, wherein the first pitch is different relative to the second pitch.

Example 4

The core needle biopsy device of Example 3, wherein the first threaded portion is configured to engage the cutter drive assembly, wherein the second threaded portion is configured to engage the piercer retraction assembly.

Example 5

The core needle biopsy device of Example 4, wherein the needle cocking assembly further includes a carriage nut disposed on the lead screw, wherein the carriage nut includes a threaded portion.

Example 6

The core needle biopsy device of Example 5, wherein the threaded portion of the carriage nut is configured to engage the piercer drive assembly.

Example 7

The core needle biopsy device of Example 6, wherein the carriage nut is axially movable with the piercer retraction assembly.

Example 8

The core needle biopsy device of Example 6, wherein the piercer drive assembly is axially movable in response to axial movement of the carriage nut.

Example 9

The core needle biopsy device of Example 6, wherein the piercer drive assembly is axially movable in response to rotational movement of the carriage nut.

Example 10

The core needle biopsy device of any one or more of Examples 1 through 9, further comprising a release assembly, wherein the release assembly is in communication with at least a portion of the cuter drive assembly and the piercer drive assembly to selectively initiate firing of the cutter and the piercer.

Example 11

The core needle biopsy device of Example 10, wherein the release assembly includes a secondary lead screw and a nut member, wherein the nut member is responsive to rotation of the secondary lead screw to initiate firing of the cutter and the piercer in a predetermined sequence.

Example 12

The core needle biopsy device of any one or more of Examples 1 through 11, wherein at least a portion of the cutter drive assembly and the piercer drive assembly is driven by a spring.

Example 13

The core needle biopsy device of any one or more of Examples 1 through 11, wherein at least a portion of the cutter drive assembly and the piercer drive assembly is driven by a motor.

Example 14

The core needle biopsy device of Example 13, wherein the motor is an electric motor.

Example 15

The core needle biopsy device of any one or more of Examples 1 through 14, wherein the piercer retraction assembly is configured to retract at least a portion of the piercer drive assembly when retracting the piercer.

Example 16

A core needle biopsy device, comprising: a body; a cutter extending from the body, wherein the cutter includes an open distal end defined by a sharp edge; a piercer disposed within the cutter, wherein the piercer comprises a notch, wherein the piercer is movable relative to the cutter to sever a tissue sample into the notch via the sharp edge; and a drive assembly, comprising; a first spring loaded mechanism, wherein the first spring loaded mechanism is in communication with the cutter to selectively fire the cutter; a second spring loaded mechanism, wherein the second spring loaded mechanism is in communication with the piercer to selectively fire the piercer; a first motor driven mechanism, wherein the first motor driven mechanism is configured to drive the first spring loaded mechanism and the second spring loaded mechanism through a first range of motion, wherein the first motor driven mechanism is further configured to drive the second spring loaded mechanism through a second range of motion while the first spring loaded mechanism remains stationary, and a second motor driven mechanism, wherein the second motor driven mechanism is in communication with the first spring loaded mechanism and the second spring loaded mechanism to selectively initiate firing of the cutter and the piercer.

Example 17

The core needle biopsy device of Example 16, wherein the cutter comprises an end portion associated with the body, wherein the end portion defines a tissue collection feature.

Example 18

The core needle biopsy device of Example 17, wherein the first motor driven mechanism is configured to drive the piercer between a distal position and a proximal position when moving second spring loaded mechanism through the second range of motion, wherein the notch of the piercer is aligned with the tissue collection feature when in the proximal position.

Example 19

The core needle biopsy device of Example 17, wherein the cutter further comprises a cutout portion, wherein the cutout portion is longitudinally aligned with the tissue collection feature.

Example 20

A method for collecting a tissue sample using a core needle biopsy device, the method comprising: firing a piercer distally from a cocked position to a distal position, wherein the piercer is disposed within a hollow cutter, wherein the piercer comprises a notice that is movable relative to a distal end of the cutter; firing the cutter distally from a cocked position to a distal position after firing the piercer to sever a first tissue sample into the notch of the piercer; retracting the piercer while the cutter remains in the distal position to collect the first tissue sample severed into the notch of the piercer; collecting the first tissue sample through a tissue window defined by the cutter; and repeating steps of firing the piercer, firing the cutter, retracting the piercer, and collecting a tissue sample to collect a second tissue sample.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

I claim:

1. A core needle biopsy device, comprising:
   (a) a needle assembly, the needle assembly including a piercer and a hollow cutter, the piercer including a sharp distal tip, the piercer being slidably disposed within the cutter to sever a tissue sample;
   (b) a cutter drive assembly configured to selectively fire the cutter;
   (c) a piercer drive assembly configured to selectively fire the piercer; and
   (d) a drive assembly configured to sequentially move both the cutter drive assembly and the piercer drive assembly, the drive assembly including a lead screw configured to translate a portion of the piercer drive assembly and the cutter drive assembly, the lead screw being further configured to retract the piercer relative to the cutter while the needle assembly is disposed within a patient to expose a distal portion of the piercer to an exterior of a patient while at least a portion of the piercer remains within the cutter;
   the lead screw being offset relative to a longitudinal axis defined by the needle assembly, and
   the lead screw including a first threaded portion and a second threaded portion, at least one of the first threaded portion or the second threaded portion being disposed on an outer surface of the lead screw.

2. The core needle biopsy device of claim 1, the first threaded portion including threads having a first pitch, the second threaded portion including threads having a second pitch, the first pitch being different relative to the second pitch.

3. The core needle biopsy device of claim 2, the first threaded portion being configured to engage the cutter drive assembly, the second threaded portion being configured to engage the piercer drive assembly.

4. The core needle biopsy device of claim 3, the drive assembly further including a carriage nut disposed on the lead screw, the carriage nut including a threaded portion.

5. The core needle biopsy device of claim 4, the threaded portion of the carriage nut being configured to engage the piercer drive assembly.

6. The core needle biopsy device of claim 5, the carriage nut being axially movable with the drive assembly.

7. The core needle biopsy device of claim 5, the piercer drive assembly being axially movable in response to axial movement of the carriage nut.

8. The core needle biopsy device of claim 5, the piercer drive assembly being axially movable in response to rotational movement of the carriage nut.

9. The core needle biopsy device of claim 1, further comprising a release assembly, the release assembly being in communication with at least a portion of the cutter drive assembly and the piercer drive assembly to selectively initiate firing of the cutter and the piercer.

10. The core needle biopsy device of claim 9, the release assembly including a rotatable member configured to move at least a portion of the release assembly to thereby initiate firing of the cutter and the piercer in a predetermined sequence.

11. The core needle biopsy device of claim 1, at least a portion of the cutter drive assembly and the piercer drive assembly being driven by a spring.

12. The core needle biopsy device of claim 1, at least a portion of the cutter drive assembly and the piercer drive assembly being driven by a motor.

13. The core needle biopsy device of claim 12, the motor being an electric motor.

14. The core needle biopsy device of claim 1, the drive assembly being configured to retract at least a portion of the piercer drive assembly when retracting the piercer.

15. A method for collecting a tissue sample using a core needle biopsy device, the method comprising:
   (a) cocking a piercer and a cutter using a single lead screw to move both the piercer and the cutter to compress a first resilient member in communication with the piercer coaxially along an axis of rotation of the single lead screw and a second resilient member in communication with the cutter coaxially along the axis of rotation of the single lead screw;
   (b) firing the piercer distally from a cocked position to a distal position, the piercer being disposed within the cutter;
   (c) firing the cutter distally from a cocked position to a distal position after firing the piercer to sever a first tissue sample using the cutter;
   (d) retracting the piercer via the single lead screw relative to the cutter to collect the first tissue sample severed by the cutter;
   (e) collecting the first tissue sample through a tissue window defined by the cutter; and
   (f) repeating steps (a)-(d) to collect a second tissue sample.

16. The method of claim 15, the step of firing the cutter including rotating a rotatable member to actuate one or more releases associated with the cutter, the piercer, or both the cutter and the piercer.

17. The method of claim 15, the step of retracting the piercer being performed using a first threading on the single lead screw, the first threading being in an opposite direction of a second threading on the single lead screw.

18. A core needle biopsy device, comprising:
   (a) a needle assembly, the needle assembly including a piercer and a hollow cutter, the piercer including a sharp distal tip, the piercer being slidably disposed within the cutter to sever a tissue sample;
   (b) a cutter carriage associated with the cutter;
   (c) a piercer carriage associated with the piercer; and
   (d) a drive assembly configured to sequentially move both the cutter carriage and the piercer carriage, the drive assembly including a dual pitch lead screw, the dual pitch lead screw being configured to translate the cutter carriage and the piercer carriage simultaneously to compress a first spring configured to drive movement of the cutter carriage and a second spring configured to drive movement of the piercer carriage, the first spring and the second spring being positioned coaxially along an axis of rotation of the dual pitch lead screw.

19. The core needle biopsy device of claim 18, the dual pitch lead screw including a first threading defining a first pitch and a second threading defining a second pitch, the first pitch being in an opposite direction of the second pitch.

\* \* \* \* \*